United States Patent [19]

Malleron et al.

[11] Patent Number: 4,886,835

[45] Date of Patent: Dec. 12, 1989

[54] ALKADIENE DERIVATIVES, THEIR PREPARATION, AND PHARMACEUTICAL COMPOSITIONS CONTAINING THEM

[75] Inventors: Jean-Luc Malleron, Marcoussis; Gerard Ponsinet, Sucy-en-Brie; Gerard Roussel, Soisy-sur-Seine, all of France

[73] Assignee: Rhone-Poulenc Sante, Antony, France

[21] Appl. No.: 248,720

[22] Filed: Sep. 26, 1988

[30] Foreign Application Priority Data

Sep. 28, 1987 [FR] France .................... 87 13357

[51] Int. Cl.$^4$ ................ A61K 31/235; A61K 31/225; C07C 149/40; C07C 149/20
[52] U.S. Cl. .................................. 514/532; 514/533; 514/545; 514/546; 514/547; 514/548; 514/549; 560/10; 560/15; 560/17; 560/152; 560/153; 560/154
[58] Field of Search .................. 560/154, 10, 15, 17, 560/121, 123, 124, 125, 152, 153; 562/431, 595, 598; 514/532, 533, 545, 546, 547, 548, 549

[56] References Cited

U.S. PATENT DOCUMENTS

4,619,945 10/1986 Loev et al. .................... 514/532

Primary Examiner—Paul J. Killos
Assistant Examiner—Julie K. Parker
Attorney, Agent, or Firm—Stevens, Davis, Miller & Mosher

[57] ABSTRACT

Substituted alkadienes of the formula:

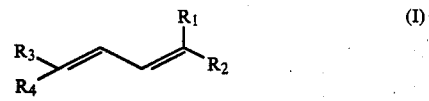

in which $R_1$ is hydroxy or acetoxy, $R_2$ is hydrogen, carboxy, alkoxycarbonyl, phenyl or benzoyl, and $R_3$ is alkylthio or alkoxy and $R_4$ is naphthoyl or optionally substituted benzoyl, or $R_3$ is alkoxycarbonyl, cycloalkyloxycarbonyl or cyano and $R_4$ is alkyl, naphthyl, optionally substituted phenyl, alkylthio, naphthylmethanethio, optionally substituted benzylthio, optionally substituted phenylthio, naphthylthio, phenethylthio or allylthio, or $R_3$ and $R_4$ form, with the carbon atom to which they are attached, a ring-system of formula:

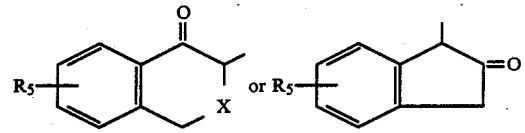

in which $R_5$ is hydrogen or alkoxy and X is methylene or S inhibit 5-lipoxygenase and are useful, for example, as anti-inflammatories.

11 Claims, No Drawings

ALKADIENE DERIVATIVES, THEIR PREPARATION, AND PHARMACEUTICAL COMPOSITIONS CONTAINING THEM

The present invention provides substituted alkadiene derivatives of the formula:

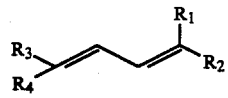

in which $R_1$ denotes hydroxy or acetoxy; $R_2$ denotes hydrogen, carboxy, alkoxycarbonyl, phenyl or benzoyl; and $R_3$ denotes alkylthio or alkoxy and $R_4$ denotes naphthoyl, benzoyl, or benzoyl substituted by one or more of halogen, alkyl, alkoxy, phenyl, phenoxy, piperidino, dimethylamino and hydroxy, or, at the 3- and 4-positions, by isopropylenedioxy; or $R_3$ denotes alkoxycarbonyl, cycloalkyloxycarbonyl in which the cycloalkyl portion contains 3 to 6 carbon atoms, or cyano, and $R_4$ denotes (a) alkyl of 1 to 8 carbon atoms, (b) naphthyl, (c) phenyl, (d) phenyl substituted by phenoxy, phenyl, naphthyl or benzoyl, (e) alkylthio, (f) naphthylmethanethio, (g) benzylthio, (h) benzylthio substituted by one or more alkyls or by trifluoromethyl, phenyl or phenoxy, (i) phenylthio, (j) phenylthio substituted by halogen or alkoxy, (k) naphthylthio, (l) phenethylthio or (m) allylthio, or $R^3$ and $R^4$ form, together with the carbon atom to which they are attached, a ring system of formula:

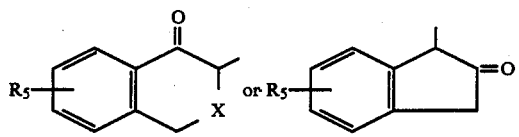

in which $R_5$ denotes hydrogen or alkoxy and X denotes methylene or sulphur with the proviso that, when $R_1$ denotes acetoxy, $R_4$ cannot denote benzoyl substituted by one or more hydroxy radicals, and that, except where otherwise stated, in the definitions above and those following, the alkyl and alkoxy radicals and alkyl and alkoxy portions contain 1 to 4 carbon atoms each in a straight or branched chain, and the tautomeric forms of the substituted alkadienes when $R_1$ denotes hydroxy.

According to the invention, the substituted alkadienes of formula (I) in which $R_1$ denotes hydroxy, $R_2$ denotes, hydrogen, alkoxycarbonyl, phenyl or benzoyl and the other symbols are defined as above are prepared by acid hydrolysis of an enamine of formula:

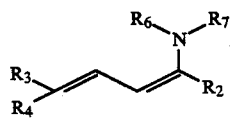

in which $R_2$ denotes hydrogen, alkoxycarbonyl, phenyl or benzoyl, $R^6$ and $R^7$ denote alkyl or $R_6$ and $R_7$ form, together with the nitrogen atom to which they are attached, a heterocycle such as a piperidine ring or a morpholine ring, and $R_3$ and $R_4$ have the same meaning as in the formula (I).

It is preferable to perform this hydrolysis in the presence of 1 to 5 equivalents of a 1N to 12N mineral acid, optionally in the presence of a water-miscible solvent, at a temperature from 20° C. to 100° C. Suitable mineral acids include hydrochloric, hydrobromic and sulphuric acids, and suitable solvents are alcohols (methanol, ethanol, propanol, isopropanol), tetrahydrofuran or dioxane.

These enamines of formula (II), except for ethyl 2-dimethylamino-5-cyano-5-phenyl-2,4-pentadienoate, are new and form part of the invention.

The enamines of formula (II) may be prepared by the action of a vinamidinium salt of formula:

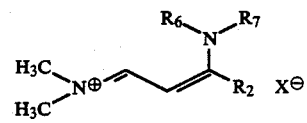

in which $R_2$, $R_6$ and $R_7$ have the same meaning as in the formula (II) and X denotes $BF_4$, Cl, $ClO_4$, Br, on a compound having an activated methylene of formula: $R_3$—$CH_2$—$R_4$, in which $R_3$ and $R_4$ have the same meaning as in the formula (II).

This reaction is performed in the presence of a base, among which sodium methylate, ethylate or tert-butylate or potassium methylate, ethylate or tert-butylate may be mentioned, in the corresponding alcohol, at a temperature of between 20° C. and the boiling point of the solvent. It is also possible to use a lithium derivative, such as methyllithium, butyllithium, lithium diisopropylamide, as a base, in an inert solvent such as tetrahydrofuran or diethyl ether, at a temperature of between −78° C. and the boiling point of the solvent.

The vinamidinium salts of formula (III) may be prepared by the action of a secondary amine $HNR_6R_7$, in which $R_6$ and $R_7$ have the same meaning as in the formula (II), on a compound of formula:

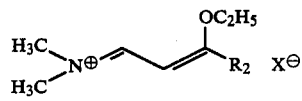

in which $R_2$ and X have the same meaning as in the formula (III).

The reaction is preferably performed in a chlorinated solvent such as chloroform, methylene chloride or 1,2-dichloroethane, at a temperature of between 0° C. and the boiling point of the solvent.

The compounds of formula (IV) may be obtained by application or adaptation of the method described by R. GOMPPER et al. Angew, Chem. Int. Ed. Eng. 17, 760–3 (1978). This method consists in reacting an alkyloxonium salt, such as triethyloxonium tetrafluoroborate, with an enamine of formula:

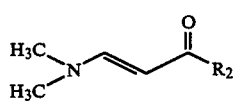

in which $R_2$ has the same meaning as in the formula (IV).

The reaction is preferably performed in a chlorinated solvent such as dichloromethane or chloroform, at a temperature of between 20° C. and the boiling point of the solvent.

The compounds of formula (V) may be obtained by application or adaptation of the methods described by R. F. ABDULLA et al. Tetrahedron 35, 1675–1734 (1979). These methods consist in reacting a dialkylacetal of N,N-dimethylformamide with a compound $CH_3$—CO—$R_2$, for which $R_2$ has the same meaning as in the formula (V).

Many compounds of formula $R_3$—$CH_2$—$R_4$ are known. Among the latter, there may be mentioned α-methoxyacetophenone (R. B. MOFFET, et al., Org. Synth., 3, 562, 1955), α-tetralone (Beil. 7, 370), 6-methoxy-1-oxo-1,2,3,4-tetrahydronaphthalene (Beil. 9(2), 889), propionitrile (Beil. 2, 245), decanenitrile (Beil. 2, 356), benzyl cyanide (Beil. 9, 441), 2-indanone (Beil. 7, 363), ethyl phenylacetate (Beil. 9, 434), 4-biphenylacetonitrile (U.S. Pat. No. 3,780,065), 3-phenoxybenzyl cyanide (D. Matthies et al., Arch. Pharm., 316, 598–608, 1938) and 3-benzoylbenzyl cyanide (A. ALLAIS et al., J. Med. Chem. Chim. Ther, 9(4), 381–389, 1974).

The new compounds of formula $R_3$—$CH_2$—$R_4$ may be obtained by application of adaptation of the methods described for the known compounds, and of the methods described below and in the examples.

The compounds of formula $R_3$—$CH_2$—$R_4$ in which $R_3$ denotes an alkoxycarbonyl or cyano radical and $R_4$ denotes a phenylthio radical optionally substituted with a halogen atom or an alkoxy radical, a naphthylthio radical, a benzylthio radical optionally substituted with one or more alkyl radicals or a trifluoromethyl, phenyl or phenoxy radical, or a phenethylthio, allylthio, alkylthio or naphthylmethanethio radical may be obtained by condensation of a thiol or a thiolate $R_8$—S—$R_9$, for which $R_8$ denotes a phenyl radical optionally substituted with a halogen atom or an alkoxy radical, a naphthyl radical, a benzyl radical optionally substituted with one or more alkyl radicals or a trifluoromethyl, phenyl or phenoxy radical, or an allyl, alkyl, naphthylmethylene or phenethyl radical, and $R_9$ denotes sodium, potassium, lithium or a hydrogen atom, with a compound of formula X—$CH_2$—$R_3$, in which X denotes a halogen atom and $R_3$ has the same meaning as above.

When $R_9$ denotes sodium, potassium or lithium, the reaction is preferably performed in a solvent such as an alcohol (methanol, ethanol, propanol, isopropanol), dimethylformamide, tetrahydrofuran or diethyl ether, at a temperature of between 0° C. and the boiling point of the solvent. The thiolates $R_8$—S—$R_9$ may be obtained by the action of a base, such as sodium methylate, ethylate or tert-butylate or potassium methylate, ethylate or tert-butylate, or a lithium-containing base such as butyllithium, on the corresponding sulphide.

When $R_9$ denotes a hydrogen atom, the reaction is preferably performed in a solvent such as methanol, ethanol, propanol, isopropanol, dimethylformamide, tetrahydrofuran or diethyl ether, or a chlorinated solvent (methylene chloride, 1,2-dichloroethane), in the presence of a tertiary base such as a trialkylamine, 1,8-diazabicyclo[5.4.0]undec-7-ene or 1,5-diazabicyclo[4.3.0]non-5-ene.

The thiols for which $R_8$ denotes a benzyl radical substituted with an alkyl, trifluoromethyl, phenyl or phenoxy radical may be obtained from the corresponding halides $R_8$—X, for which $R_8$ has the same meaning as above and X denotes a halogen atom, by the action of sodium hydrosulphide, by processes that are known per se, such as those described by MARCH, Advanced Organic Chemistry, 1977, p. 374 (second edition). The halides $R_8$—X may be obtained by application or adaptation of the methods described by J. ASHBY et al., Carcinogenesis, 2(1), 33–38, 1981, D. MATTHIES et al., Arch. Pharm., 316, 598–608, 1983, J. L. RIDEOUT et al., J. Med. Chem. 1489, 1983 and in Beil. 5, 364, 373 and 384.

The compounds of formula $R_3$—$CH_2$—$R_4$ in which $R_3$ denotes an alkoxycarbonyl radical and $R_4$ denotes a benzylthio radical optionally substituted with a phenyl, phenoxy, alkyl or trifluoromethyl radical may be obtained by the condensation of ethyl mercaptoacetate with a compound of formula X-$R_{10}$, in which X denotes a halogen atom and $R_{10}$ denotes a benzyl radical optionally substituted with a phenyl, phenoxy, alkyl or trifluoromethyl radical.

The reaction is preferably performed in a solvent such as an alcohol (methanol, ethanol, propanol, isopropanol), dimethylformamide, tetrahydrofuran or diethyl ether, in the presence of a base such as sodium methylate, ethylate or tert-butylate or potassium methylate, ethylate or tert-butylate, or a lithium-containing base such as butyllithium, on ethyl mercaptoacetate at a temperature of between 0° C. and the boiling point of the solvent.

The compounds of formula $R_3$—$CH_2$—$R_4$ in which $R_3$ denotes an alkoxycarbonyl or cycloalkyloxycarbonyl radical and $R_4$ denotes a (1–8C) alkyl or naphthyl radical, the phenyl radical optionally substituted with a phenoxy, phenyl, naphthyl or benzoyl radical, an alkylthio or naphthylmethanethio radical, a benzylthio radical optionally substituted with one or more alkyl radicals or a trifluoromethyl, phenyl or phenoxy radical, a phenylthio radical optionally substituted with a halogen atom or an alkoxy radical, or a naphthylthio, phenethylthio or allylthio radical may be prepared by esterification of the corresponding acids by processes that are known per se, such as those described by MARCH, Advanced Organic Chemistry, 1977, p. 363–367 (second edition).

Preferably, the esterification is performed by means of an alcohol in the presence of a mineral acid.

The acids for which $R_4$ denotes a phenyl radical optionally substituted with a phenoxy, phenyl, naphthyl or benzoyl radical may be obtained by application or adaptation of the methods described by D. MATTHIES et al., Arch. Pharm., 316, 598–608, 1983; A ALLAIS et al., Eur. J. Med. Chem. Chim. Ther., 9(4), 381–389, 1974 and R. M. SHAFIF et al., J. Pharm. Sci, 952–955, 1969.

The acids for which $R_3$ denotes a carboxy radical and $R_4$ denotes an alkylthio or naphthylmethanethio radical, a benzylthio radical optionally substituted with one or more alkyl radicals or a trifluoromethyl, phenyl or phenoxy radical, a phenylthio radial optionally substituted with a halogen atom or an alkoxy radical, or a naphthylthio, phenethylthio or allylthio radical may be prepared by hydrolysis of the corresponding ethyl esters or cyano derivatives described above, by processes that are known per se, such as those described by MARCH, Advanced Organic Chemistry, 1977, p. 349–354 (second edition).

The compounds of formula $R_3$—$CH_2$—$R_4$ in which $R_3$ denotes an alkylthio radical and $R_4$ denotes a naphthoyl or benzoyl radical or a benzoyl radical substituted with one or more halogen atoms or one or more alkyl, alkoxy, phenyl, phenoxy, hydroxy, piperidino or dimethylamino radicals, or, at the 3- and 4-positions, with an isopropylenedioxy radical, may be prepared by the action of the compounds $R_{11}$—SNa, for which $R_{11}$ denotes an alkyl radical, on a halide of formula R₄—CH₂—X, in which R₄ has the same meaning as above and X denotes a halogen atom. This reaction is preferably performed in an alcohol such a methanol or ethanol, at a temperature of between 20° C. and 60° C.

The chloride of formula R₄—CH₂Cl in which R₄ denotes a benzoyl radical substituted with a piperidine radical may be prepared by the action of titanium (III) chloride on the dibrominated derivative R₄—CO—CH—Br₂, for which R₄ has the same meaning as above, in the presence of a mineral acid such as hydrochloric acid, at a temperature of approximately 100° C.

The compound of formula R₄—CO—CH—Br₂ may be obtained by the action of a bromine/hydrobromic acid mixture on the corresponding keto derivative, preferably at 20° C.

The other new halides of formula R⁴—CH₂—X may be prepared by halogenation of the corresponding compounds R₄—CH₃ by methods that are known per se, such as those described by MARCH, Advanced Organic Chemistry, 1977, p. 537–39 (second edition) or by adaptation of the methods for the preparation of known halides.

The compounds R₁₁—SNa may be obtained by the action of a base, such as sodium methylate or ethylate, on the corresponding thiol.

The compounds of formula R₃—CH₂—R₄ in which R₃ denotes an alkoxy radical and R₄ denotes a naphthoyl or benzoyl radical or a benzoyl radical substituted with one or more halogen atoms or one or more phenyl, phenoxy, hydroxy, piperidino or dimethylamino radicals, or, at the 3- and 4-positions, with an isopropylenedioxy radical may be obtained by application or adaptation of the method described by R. B. MOFFET et al., Org. Synth., 3, 562 (1955).

The compounds of formula:

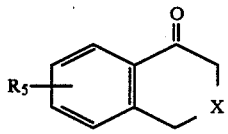

in which R₅ denotes a hydrogen atom or an alkoxy radical and X denotes a sulphur atom may be obtained by heating benzylthioacetic acid, where appropriate substituted with an alkoxy radical, in a solvent such as nitrobenzene, in the presence of an acid such as polyphosphoric acid, at a temperature of between 50° and 180°0 C.

According to the invention, the products of formula (I) in which R₁ denotes a hydroxyl radical, R₂ denotes an alkoxycarbonyl radical and the other symbols are defined as above, may also be prepared by acid hydrolysis of the enamines of formula:

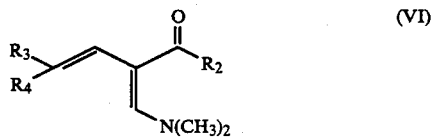

in which R₂ denotes an alkoxycarbonyl radical and R₃ and R₄ have the same meaning as in the formula (I).

This hydrolysis may be performed under the same working conditions as the hydrolysis of the enamines of formula (II).

The enamines of formula (VI) may be obtained by the action of a dialkylacetal N,N-dimethylformamide on a corresponding acid of formula (I) in which R₂ denotes a carboxy radical, R₁ denotes a hydroxy radical and R₃ and R₄ are defined as above. It is preferable to work in a chlorinated solvent such as chloroform or dichloromethane, at a temperature in the region of 20° C.

The enamines of formula (VI) are new, and form part of the invention.

According to the invention, the products of formula (I) in which R₁ denotes a hydroxy radical, R₂ denotes a carboxy radical and the other symbols are defined as above may be prepared by saponification of the corresponding enol ester of formula:

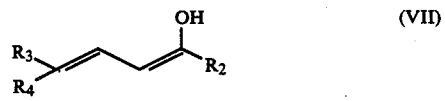

in which R₂ denotes an alkoxycarbonyl radical and R₃ and R₄ are defined as above.

Preferably, this reaction is performed using 2 to 10 equivalents of 1N to 4N sodium hydroxide or potassium hydroxide, optionally in the presence of a water-miscible inert solvent such as methanol, ethanol, propanol, isopropanol or tetrahydrofuran, at a temperature of between 20° C. and 50° C.

According to the invention, the products of formula (I) in which R₁ denotes an acetoxy radical and the other symbols are defined as above, on the understanding that R₃ cannot denote a benzoyl radical substituted with one or more hydroxy radicals, may be obtained by the action of acetyl chloride on the corresponding enol of formula (I), in which R₁ denotes a hydroxy radical. This reaction is preferably performed in an inert solvent such as tetrahydrofuran, in the presence of an acceptor for acid such as triethylamine, at a temperature of approximately 20° C.

The reaction mixtures obtained by the various processes described above are treated according to traditional physical methods (evaporation, extraction, distillation, crystallization, chromatography) or traditional chemical methods.

The compounds of formula (I) possess advantageous pharmacological properties. These compounds inhibit 5-lipoxygenase, and are hence useful as antiinflammatories, as protective agents, in particular, with respect to the gastrointestinal tract, and for the treatment of asthma, allergic conditions, psoriasis, rheumatoid arthritis and fibrosis, in particular hepatic fibrosis.

The inhibition of 5-lipoxygenase was determined on RBL-1 cells according to the methods of M. M. STEINHOFF et al., B.B.B., 618, 28–34, 1980 and B. A. JAKSCHIK et al., J. Biol. Chem., 257, 5346, 1982. In this test, the IC₅₀(M) of the compounds of formula (I) is between $10^{-5}$ and $10^{-7}$.

These compounds are also active with respect to PMN cells, according to the method of H. SAFAYHI et al, Biochem. Pharmacol., 34(15), 2691–4, 1985. In this test, the IC₅₀(M) of the compounds of formula (I) is between $10^{-5}$ and $10^{-7}$.

The products of formula (I) possess low toxicity. Their oral LD₅₀ is greater than 100 mg/kg in mice.

The following compounds are especially useful:
—the compounds of formula (I) in which
either R₁ denotes a hydroxy radical, R₂ denotes an alkoxycarbonyl radical, R₃ denotes an alkylthio radical and R$_4$ denotes a benzoyl radical substituted with a halogen atom, a piperidino radical or two hydroxy radicals, or, at the 3- and 4-positions, with an isopropylenedioxy radical;

or R$_1$ denotes a hydroxy or acetoxy radical, R$_2$ denotes a hydrogen atom or a carboxy, alkoxycarbonyl or phenyl radical, R$_3$ denotes an alkoxycarbonyl radical and R$_4$ denotes an alkylthio radical or a benzylthio radical optionally substituted with an alkoxy radical.
—and the tautomeric forms of these products when R$_1$ denotes a hydroxy radical.

The following products are especially useful:
2-hydroxy-5-phenylthio-5-ethoxycarbonyl-2,4-pentadienoic acid,
ethyl 6-(4-chlorophenyl)-2-hydroxy-5-methylthio-6-oxo-2,4-hexadienoate,
ethyl 2-hydroxy-5-methylthio-6-oxo-6-(4-piperidinophenyl)-2,4-hexadienoate,
diethyl 2-hydroxy-5-(4-methoxyphenylthio)-2,4-hexadienedioate,
diethyl 5-benzylthio-2-hydroxy-2,4-hexadienedioate,
ethyl 5-hydroxy-2-phenylthio-2,4-pentadienoate,
diethyl 2-acetoxy-5-phenylthio-2,4-hexadienedioate,
ethyl 5-oxo-5-phenyl-2-phenylthio-2-pentenoate,
ethyl 2-hydroxy-6-(3,4-isopropylenedioxyphenyl)-5-methylthio-6-oxo-2,4-hexadienoate,
ethyl 2-hydroxy-5-methoxy-6-oxo-6-phenyl-2,4-hexadienoate,
diethyl 2-hydroxy-5-methylthio-2,4-hexadienedioate, and
diethyl 2-hydroxy-5-ethylthio-2,4-hexadienedioate.

The examples which follow illustrate the invention.

EXAMPLE 1

1N aqueous sodium hydroxide solution (211 cc) is added in the course of 10 minutes, while a temperature in the region of 20° C. is maintained, to an ethanolic solution of diethyl 2-hydroxy-5-phenylthio-2,4-hexadienedioate (17 g). The mixture is maintained at a temperature in the region of 20° C. for 2 hours 15 minutes, and is then brought to pH 1 using 1N aqueous hydrochloric acid solution.

The reaction ethanol is evaporated off under reduced pressure (20 mm Hg; 2.7 kPa). After the addition of water (100 cc), the mixture is extracted with ethyl acetate (2×150 cc). The organic phase is dried over anhydrous magnesium sulphate and concentrated to dryness at 40° C. under reduced pressure (20 mm Hg; 2.7 kPa). The solid thereby obtained is recrystallized in a boiling mixture of isopropyl ether and acetonitrile (50:50 by volume).

2-Hydroxy-5-phenylthio-5-ethoxycarbonyl-2,4-pentadienoic acid (9.5 g), m.p. 172° C., is thereby obtained.

EXAMPLE 2

1N aqueous hydrochloric acid solution (344 cc) is added in the course of 10 minutes, while the temperature is maintained at approximately 40° C., to a solution of diethyl 2-dimethylamino-5-phenylthio-2,4-hexadienedioate (60 g) in ethanol (340 cc). The suspension obtained is cooled to a temperature of approximately 20° C., and is maintained for 30 minutes at this temperature. The precipitate is filtered off, washed with water (3×50 cc) and dried at 20° C. under reduced pressure (20 mm Hg; 2.7 kPa) in the presence of phosphoric anhydride. A crystalline solid (54 g) is obtained. 13 g of this solid are recrystallized in boiling isopropyl ether (30 cc). Diethyl 2-hydroxy-5-phenylthio-2,4-hexadienedioate (10 g), m.p. 98° C., is thereby obtained.

Diethyl 2-dimethylamino-5-phenylthio-2,4-hexadienedioate may be obtained in the following manner:

A 2M ethanolic solution of sodium ethylate (210 cc) is added dropwise, in the course of 50 minutes and while the temperature is maintained at approximately 20° C., to a solution of ethyl (phenylthio)acetate (68.7 g) and N-(3-dimethylamino-3-ethoxycarbonylpropenylidene)-N-methylmethanaminium tetrafluoroborate (100 g) in ethanol (120 cc). The reaction mixture is maintained for 2 hours 20 minutes at a temperature in the region of 20°, and the solvent is then distilled off under reduced pressure (20 mm Hg; 2.7 kPa) at 40° C. The residue is taken up with distilled water (1,000 cc) and extracted with ethyl acetate (3×300 cc). After being washed with water, the organic extracts are dried over anhydrous magnesium sulphate and concentrated to dryness under reduced pressure (20 mm Hg; 2.7 kPa). After recrystallization in boiling isopropyl ether (150 cc), a solid (107 g), m.p. 70° C., is obtained.

15 g of this solid are chromatographed on a column 6 cm in diameter containing silica (450 g), with a cyclohexane/ethyl acetate mixture (80:20 by volume) as eluent. The first fraction (800 cc) is discarded and fractions (100 cc) are then collected. Fractions 4 to 11 are combined and concentrated to dryness at 40° C. under reduced pressure (20 mm Hg; 2.7 kPa). After recrystallization in boiling isopropyl ether (40 cc), diethyl 2-dimethylamino-5-phenylthio-2,4-hexadienedioate (13.2 g), m.p. 76° C., is obtained.

N-(3-Dimethylamino-3-ethoxycarbonylpropenylidene)-N-methylmethanaminium tetrafluoroborate may be obtained in the following manner:

A solution of dimethylamine (233 cc) in methylene chloride is added in the course of 1 hour 20 minutes, at a temperature of approximately 20° C., to a solution of N-(3-ethoxy-3-ethoxycarbonylpropenylidene)-N-methylmethanaminium tetrafluoroborate (1,007 g) in methylene chloride. Anhydrous ethyl ether (2,000 cc) is then run slowly into the reaction medium, and the crystalline product is then separated off by filtration and dried under reduced pressure (20 mm Hg; 2.7 kPa) at a temperature of approximately 20° C. N-(3-Dimethylamino-3-ethoxycarbonylpropenylidene)-N-methylmethanaminium tetrafluoroborate (925 g), m.p. 102° C., is thereby obtained.

N-(3-Ethoxy-3-ethoxycarbonylpropenylidene)-N-methylmethanaminium tetrafluoroborate may be obtained in the following manner:

Ethyl 4-dimethylamino-2-oxo-3-butenoate (675 g) is added in the course of 3 hours, while the temperature is maintained at approximately 10° C., to a solution, cooled to 10° C. and through which a stream of argon is passed, of triethyloxonium tetrafluoroborate (862 g) in methylene chloride. The reaction medium is then stirred for 5 hours at a temperature in the region of 20° C. The solution of N-(3-ethoxy-3-ethoxycarbonylpropenylidene)-N-methylmethanaminium tetrafluoroborate thereby obtained is stored under an argon atmosphere, and is used immediately in the subsequent syntheses.

Ethyl 4-dimethylamino-2-oxo-3-butenoate may be obtained in the following manner:

Ethyl pyruvate (1,500 g) is added in the course of 2 hours, while the temperature is maintained at approximately 5° C., to N,N-dimethylformamide diethyl acetal (2,100 g) cooled to a temperature in the region of 5° C.

The mixture is then stirred for 3 hours at a temperature in the region of 20° C. The reaction ethanol is evaporated off to dryness and the residue obtained is pounded with diethyl ether (12 liters) and charcoal 3S (30 g) and then filtered on supercel. The filtrate is taken up with water (500 cc), and the organic phase is decanted and the aqueous phase is extracted with dichloromethane (3×2000 cc). The organic phases are mixed, dried over sodium sulphate, filtered and concentrated to dryness at 40° C. under reduced pressure (20 mm Hg; 2.7 kPa). The oil obtained is purified by distillation (b.p.$_{0.1\ mm\ Hg}$ 146°–149° C.). Ethyl 4-dimethylamino-2-oxo-3-butenoate (695 g) is thereby obtained, and is used in the crude state in the subsequent syntheses.

Ethyl (phenylthio)acetate may be obtained in the following manner:

Thiophenol (300 g) is added dropwise in the course of 10 minutes, at a temperature in the region of 20° C., to a 2M ethanolic solution (1,400 cc) of sodium ethylate. Ethyl bromoacetate (454 g) is then introduced while the temperature is maintained at approximately 10° C. The precipitate obtained is filtered off and the residual ethanolic solution is concentrated to dryness at 40° C. under reduced pressure (20 mm Hg; 2.7 kPa). The residue is distilled and ethyl (phenylthio)acetate (352 g), the b.p. of which is 125° C. under 0.75 mm Hg (0.1 kPa), is obtained.

EXAMPLE 3

1N aqueous hydrochloric acid solution (70 cc) is added in the course of 2 minutes to a solution, maintained under reflux, of ethyl 2-dimethylamino-4-(1-oxo-1,2,3,4-tetrahydro-2-naphthylidene)-2-butenoate (21 g) in ethanol (150 cc). The mixture is immediately cooled to a temperature in the region of 20° to 30° C., and the reaction ethanol is distilled off at 40° C. under reduced pressure (20 mm Hg; 2.7 kPa). The suspension obtained is diluted with water (50 cc), and extracted with ethyl acetate (2×50 cc). After being washed with water (50 cc) and dried, the organic phase is concentrated to dryness at 40° C. under reduced pressure (20 mm Hg; 2.7 kPa). After recrystallization of the solid obtained in a boiling isopropyl ether/ethyl acetate mixture (90:10 by volume), ethyl 2-hydroxy-4-(1-oxo-1,2,3,4-tetrahydro-2-naphthylidene)-2-butenoate (11.2 g), m.p. 117° C., is obtained.

Ethyl 2-dimethylamino-4-(1-oxo-1,2,3,4-tetrahydro-2-naphthylidene)-2-butenoate may be obtained in the following manner:

α-Tetralone (51 g) is added dropwise in the course of 45 minutes, at a temperature in the region of 15° C., to a mixture of N-(3-dimethylamino-3-ethoxycarbonyl-propenylidene)-N-methylmethanaminium tetrafluoroborate (100 g) in ethanol (500 cc) and a 2M ethanolic solution of sodium ethylate (210 cc). The mixture is maintained for 1 hour 45 minutes at a temperature in the region of 20° C. and is then heated for 4 hours 45 minutes to 70° C. The reaction ethanol is evaporated off to dryness and the oil obtained is pounded with ethyl ether (4×300 cc). The ethereal extracts are concentrated to dryness under reduced pressure (20 mm Hg; 2.7 kPa). After recrystallization of the solid obtained in a boiling mixture (60 cc) of isopropyl ether and ethyl acetate (90:10 by volume), ethyl 2-dimethylamino-4-(1-oxo-1,2,3,4-tetrahydro-2-naphthylidene)-2-butenoate (17.5 g), m.p. 84° C., is obtained.

EXAMPLE 4

1N aqueous hydrochloric acid solution (53 cc) is added, in the course of 10 minutes and while refluxing is maintained, to a solution of ethyl 6-phenyl-6-oxo-5-methylthio-2-dimethylamino-2,4-hexadienoate (13 g) in ethanol (100 cc). The mixture is immediately cooled and the reaction ethanol is concentrated to 40° C. under reduced pressure (20 mm Hg; 2.7 kPa). The suspension obtained is diluted with dis-tilled water (100 cc) and extracted with diethyl ether (3×100 cc). After being washed with water, the organic extracts are concentrated to dryness at 40° C. under reduced pressure (20 mm Hg; 2.7 kPa). After recrystallization of the solid obtained in boiling isopropyl ether (45 cc), ethyl 6-phenyl-6-oxo-5-methylthio-2-hydroxy-2,4-hexadienoate (10.2 g), m.p. 86° C., is obtained.

Ethyl 6-phenyl-6-oxo-5-methylthio-2-dimethylamino-2,4-hexadienoate may be obtained in the following manner:

A 2M ethanolic solution of sodium ethylate (54 cc) is added dropwise in the course of 30 minutes to a solution, maintained at a temperature in the region of 25° C., of N-(3-dimethylamino-3-ethoxycarbonyl-propenylidene)-N-methylmethanaminium tetrafluoroborate (26 g) and α-methylthioacetophenone (30 g) in ethanol (100 cc). The mixture is maintained for 2 hours 10 minutes at a temperature in the region of 25° C., and the reaction ethanol is then removed by distillation at 40° C. under reduced pressure (20 mm Hg; 2.7 kPa). After recrystallization of the residue in boiling isopropyl ether (100 cc), ethyl 6-phenyl-6-oxo-5-methylthio-2-dimethylamino-2,4-hexadienoate (19.2 g), m.p. 78° C., is obtained.

α-Methylthioacetophenone may be obtained in the following manner:

Sodium methanethiolate (70 g) is added in small portions, in the course of 1 hour 30 minutes and at a temperature in the region of 20° C., to a solution of α-bromoacetophenone (199 g) in ethanol (500 cc). The mixture is maintained for 2 hours 30 minutes at a temperature in the region of 20° C. The suspended solid is removed by filtration and the reaction ethanol is removed by evaporation to dryness at 40° C. under reduced pressure (20 mm Hg; 2.7 kPa). The oily residue is taken up with diethyl ether (400 cc), and the organic phase is washed with water (4×200 cc), dried and concentrated to dryness at 40° C. under reduced pressure (20 mm Hg; 2.7 kPa). After distillation, α-methylthioacetophenone (98 g), which distils at 100°–102° C. under a pressure of 0.2 mm Hg (0.027 kPa), is obtained.

EXAMPLE 5

1N aqueous hydrochloric acid solution (87 cc) is added in the course of 3 minutes to a solution, maintained under reflux, of ethyl 2-dimethylamino-5-cyano-5-phenyl-2,4-pentadienoate (21.3 g) in ethanol (27 cc). The mixture is cooled to a temperature of approximately 10° C. and the precipitate obtained is filtered off, washed with ethanol (15 cc) and dried. Ethyl 2-hydroxy-5-cyano-5-phenyl-2,4-pentadienoate (12.1 g), m.p. 189° C., is thereby obtained.

Ethyl 2-dimethylamino-5-cyano-5-phenyl-2,4-pentadienoate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (57.2 g), a 2M ethanolic solution of sodium ethylate (105 cc) and benzyl cyanide (23.4 g). Ethyl 2-dimethylamino-5-cyano-5-phenyl-2,4-pentadienoate (36.1 g), m.p. 67° C., is obtained.

EXAMPLE 6

Normal aqueous hydrochloric acid solution (34 cc) is added to a stirred solution, heated for 15 minutes to 50° C., of 6-ethyl 1-methyl 3-(dimethylaminomethylene)-2-oxo-5-phenylthio-4-hexenedioate (6.3 g) in ethanol (70 cc). Stirring is continued for 2 hours at a temperature in the region of 20° C. The solution is concentrated to dryness at 40° C. under reduced pressure (20 mm Hg; 2.7 kPa). The residue is washed with water and then taken up with dichloromethane (100 cc). The organic phase is dried over anhydrous magnesium sulphate, filtered and concentrated to dryness at 40° C. under reduced pressure (20 mm Hg; 2.7 kPa). The oil obtained is recrystallized in boiling isopropyl ether (60 cc). 6-Ethyl 1-methyl 2-hydroxy-5-phenylthio-2,4-hexadienedioate (2.7 g), m.p. 112° C., is thereby obtained.

6-Ethyl 1-methyl-3-(dimethylaminomethylene)-2-oxo-5-phenylthio-4-hexenedioate may be obtained in the following manner:

2-Hydroxy-5-phenylthio-5-ethoxycarbonyl-2,4-pentadienoic acid (8 g), obtained according to Example 1, N,N-dimethylformamide dimethyl acetal (7.2 cc) and dichloromethane (80 cc) are stirred for 2 hours at a temperature in the region of 20° C. The solution is concentrated to dryness at 40° C. under reduced pressure (20 mm Hg; 2.7 kPa). A residue is obtained, which is dissolved in a mixture (100 cc) of cyclohexane and ethyl acetate (90:10 by volume). The solution is poured onto silica (500 g) contained in a column 5 cm in diameter. Elution is performed with a mixture of cyclohexane and ethyl acetate (90:10 by volume) and the corresponding eluate is concentrated to dryness at 40° C. under reduced pressure (20 mm Hg; 2.7 kPa). 6-Ethyl 1-methyl 3-(dimethylaminomethylene)-2-oxo-5-phenylthio-4-hexenedioate (5.6 g), m.p. 118° C., is thereby obtained.

EXAMPLE 7

The procedure is as in Example 3, starting with ethyl 2-dimethylamino-4-(6-methoxy-1-oxo-1,2,3,4-tetrahydro-2-naphthylidene)-2-butenoate (4.2 g), 1N aqueous hydrochloric acid solution (19.1 cc) and ethanol (19 cc). The mixture is heated to boiling for 5 minutes, and then cooled to a temperature in the region of 20° C. After purification by recrystallization in boiling ethanol (120 cc), ethyl 2-hydroxy-4-(6-methoxy-1-oxo-1,2,3,4-tetrahydro-2-naphthylidene)-2-butenoate (3.4 g), m.p. 175° C., is obtained.

Ethyl 2-dimethylamino-4-(6-methoxy-1-oxo-1,2,3,4-tetrahydro-2-naphthylidene)-2-butenoate may be prepared in the following manner:

The procedure is as in Example 3 for the preparation of ethyl 2-dimethylamino-4-(1-oxo-1,2,3,4-tetrahydro-2-naphthylidene)-2-butenoate, starting with N-(3-dimethylamino-3-ethoxycarbonylpropenylidene)-N-methylmethanaminium tetrafluoroborate (14.3 g), a 2M ethanolic solution of sodium ethylate (30 cc) and 6-methoxy-1-oxo-1,2,3,4-tetrahydronaphthalene (8.8 g) in ethanol (72 cc). After purification by chromatography on a silica column with a mixture of cyclohexane and ethyl acetate (50:50 by volume) as eluent, and precipitation in ethyl ether (150 cc), ethyl 2-dimethylamino-4-(1-oxo-1,2,3,4-tetrahydro-2-naphthylidene)2-butenoate (7.2 g), m.p. 123° C., is obtained.

EXAMPLE 8

The procedure is as in Example 3, starting with ethyl 2-dimethylamino-4-(2-oxo-2,3-dihydro-1-indenylidene)-2-butenoate (3.8 g), 1N aqueous hydrochloric acid solution (20 cc) and ethanol (20 cc). The mixture is heated for 10 minutes to a temperature in the region of 60° C., and is then cooled to approximately 20° C. After purification by chromatography on a silica column with a mixture of cyclohexane and ethyl acetate (70:30 by volume) as eluent, and recrystallization in a boiling mixture (52 cc) of cyclohexane and ethanol (90:10 by volume), ethyl 2-hydroxy-4-(2-oxo-2,3-dihydro-1-indenylidene)-2-butenoate (1.5 g), m.p. 137° C., is obtained.

Ethyl 2-dimethylamino-4-(2-oxo-2,3-dihydro-1-indenylidene)-2-butenoate may be prepared in the following manner:

The procedure is as in Example 3 for the preparation of ethyl 2-dimethylamino-4-(1-oxo-1,2,3,4-tetrahydro-2-naphthylidene)-2-butenoate, starting with N-(3-dimethylamino-3-ethoxycarbonylpropenylidene)-N-methylmethanaminium tetrafluoroborate (14.3 g), a 1.6M solution (31.2 cc) of butyllithium in hexane and 2-indanone (6.6 g) in tetrahydrofuran (100 cc) at a temperature in the region of 0° C. After purification by chromatography on a silica column with a mixture of cyclohexane and ethyl acetate (50:50 by volume) as eluent, and recrystallization in boiling isopropyl ether (70 cc), ethyl 2-dimethylamino-4-(2-oxo-2,3-dihydro-1-indenylidene)-2-butenoate (4.9 g), m.p. 93°–95° C., is obtained.

EXAMPLE 9

The procedure is as in Example 3, starting with ethyl 2-dimethylamino-4-(1-oxo-3-thia-1,2,3,4-tetrahydro-2-naphthylidene)-2-butenoate (16.8 g), 1N aqueous hydrochloric acid solution (120 cc) and ethanol (120 cc). The mixture is stirred for 15 hours at a temperature in the region of 20° C. After purification by chromatography on a silica column with dichloromethane as eluent, and recrystallization in boiling isopropanol (40 cc), ethyl 2-hydroxy-4-(1-oxo-3-thia-1,2,3,4-tetrahydro-2-naphthylidene)-2-butenoate (1.5 g), m.p. 152° C., is obtained.

Ethyl 3-dimethylamino-4-(1-oxo-3-thia-1,2,3,4-tetrahydro-2-naphthylidene)-2-butenoate may be prepared in the following manner:

The procedure is as in Example 3 for the preparation of ethyl 2-dimethylamino-4-(1-oxo-1,2,3,4-tetrahydro-2-naphthylidene)-2-butenoate, starting with N-(3-dimethylamino-3-ethoxycarbonylpropenylidene)-N-methylmethanaminium tetrafluoroborate (15.2 g), a 2M ethanolic solution of sodium ethylate (35 cc) and 1-oxo-3-thia-1,2,3,4-tetrahydronaphthalene (8.7 g) in ethanol (160 cc). Ethyl 2-dimethylamino-4-(1-oxo-3-thia-1,2,3,4-tetrahydro-2-naphthylidene)-2-butenoate (13 g) is obtained, and is used in the crude state in the subsequent syntheses.

1-Oxo-3-thia-1,2,3,4-tetrahydronaphthalene may be prepared according to the following process:

Nitrobenzene (975 cc) and polyphosphoric acid (292.5 g) are heated to a temperature in the region of 70° C. (Benzylthio)acetic acid (97.5 g) is added to the reaction medium. The mixture is left with stirring for 26 hours at approximately 70° C., and then cooled to approximately 20° C. Saturated aqueous sodium bicarbonate solution (4,000 cc) and dichloromethane (4,000 cc) are added to the solution. The organic phase is separated off after settling has taken place, and the aqueous phase is extracted with dichloromethane (2×200 cc). The organic phases are combined, dried over anhydrous magnesium sulphate, filtered and evaporated at 40° C. under reduced pressure (20 mm Hg; 2.7 kPa). The residue is dissolved in a mixture (80 cc) of cyclohexane and ethyl acetate (85:15 by volume), and the solution is poured onto silica (2 kg) contained in a column 9 cm in diameter. Elution is performed with a mixture of cyclohexane and ethyl acetate (85:15 by volume); the corresponding eluate is concentrated to dryness at 40° C. under reduced pressure (20 mm Hg; 2.7 kPa). 1-Oxo-3-thia-1,2,3,4-tetrahydronaphthalene (10 g) is thereby obtained, and is used in the crude state in the subsequent syntheses.

(Benzylthio)acetic acid may be prepared in the following manner:

1N aqueous sodium hydroxide solution (500 cc), cooled to a temperature of approximately 5° C., is added in the course of 1 hour to bromoacetic acid (70 g). The mixture obtained is added to a solution of phenylmethanethiol (50 g) and 1N aqueous sodium hydroxide solution (500 cc) in tetrahydrofuran (500 cc), and then heated to approximately 100° C. for 90 minutes. The mixture is cooled to a temperature in the region of 5° C. There are added 12N aqueous hydrochloric acid solution (100 cc) and then dichloromethane (3,000 cc) in the course of 30 minutes. The organic phase is separated off after settling has taken place, and the aqueous phase is extracted with dichloromethane (2×200 cc). The organic phases are combined, dried over anhydrous magnesium sulphate, filtered and evaporated to dryness at 40° C. under reduced pressure (20 mm Hg; 2.7 kPa). The residue is recrystallized in boiling cyclohexane (50 cc). (Benzylthio)acetic acid (40.5 g), m.p. 58°–60° C., is obtained.

EXAMPLE 10

The procedure is as in Example 2, starting with 1-ethyl 6-methyl 2-dimethylamino-5-phenylthio-2,4-hexadienedioate (6 g) and 12N aqueous hydrochloric acid solution (30 cc). The mixture is heated to boiling for 1 minute, and is then cooled to a temperature of approximately 20° C. After purification by recrystallization in boiling cyclohexane (50 cc), 1-ethyl 6-methyl 2-hydroxy-5-phenylthio-2,4-hexadienedioate (4.3 g), m.p. 85° C., is obtained.

1-Ethyl 6-methyl 2-dimethylamino-5-phenylthio-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (8.6 g), a 1.6M solution (18.7 cc) of butyllithium in hexane and methyl (phenylthio)acetate (5.5 g) in tetrahydrofuran (50 cc) at a temperature in the region of 0° C. After purification by chromatography on a silica column with dichloromethane as eluent, and recrystallization in boiling cyclohexane (90 cc), 1-ethyl 6-methyl 2-dimethylamino-5-phenylthio-2,4-hexadienedioate (6.8 g), m.p. 75° C., is obtained.

Methyl (phenylthio)acetate may be prepared in the following manner:

Phenylthioacetic acid (16 g) and 36N aqueous sulphuric acid solution (0.26 cc) in methanol (80 cc) are brought to boiling for 24 hours. After cooling to approximately 20° C., potassium carbonate (1 g) is added to the reaction medium. The organic phase is dried over anhydrous magnesium sulphate, filtered and concentrated to dryness at 50° C. under reduced pressure (20 mm Hg; 2.7 kPa). The oil is dissolved in a mixture (20 cc) of cyclohexane and ethyl acetate (50:50 by volume) and the solution is poured onto silica (700 g) contained in a column 7 cm in diameter. Elution is performed with a mixture of cyclohexane and ethyl acetate (50:50 by volume); the corresponding eluate is concentrated to dryness at 40° C. under reduced pressure (20 mm Hg; 2.7 kPa). Methyl (phenylthio)acetate (11 g) is thereby obtained, and is used in the crude state in the subsequent syntheses.

EXAMPLE 11

The procedure is as in Example 4, starting with ethyl 6-(4-chlorophenyl)-2-dimethylamino-5-methylthio-6-oxo-2,4-hexadienoate (7.8 g) and 1N aqueous hydrochloric acid solution (33 cc) in ethanol (300 cc). The mixture is heated to boiling for 5 minutes, and then cooled to a temperature in the region of 20° C. After purification by recrystallization in boiling cyclohexane (70 cc), ethyl 6-(4-chlorophenyl)-2-hydroxy-5-methylthio-6-oxo-2,4-hexadienoate (5.6 g), m.p. 88° C., is obtained.

Ethyl 6-(4-chlorophenyl)-2-dimethylamino-5-methylthio-6-oxo-2,4-hexadienoate may be prepared in the following manner:

The procedure is as in Example 4 for the preparation of ethyl 6-phenyl-6-oxo-5-methylthio-2-dimethylamino-2,4-hexadienoate, starting with N-(3-dimethylamino-3-ethoxycarbonylpropenylidene)-N-methylmethanaminium tetrafluoroborate (11.3 g), a 2M ethanolic solution of sodium ethylate (19.7 cc) and α-methylthio-4-chloroacetophenone (7.9 g) in ethanol (86 cc). After purification by recrystallization in boiling cyclohexane (130 cc), ethyl 6-(4-chlorophenyl)-2-dimethylamino-5-methylthio-6-oxo-2,4-hexadienoate (7.8 g), m.p. 93° C., is obtained.

α-Methylthio-4-chloroacetophenone may be prepared in the following manner:

Sodium methanethiolate (3.5 g) is added in the course of 15 minutes at a temperature in the region of 20° C. to a stirred solution of α-bromo-4-chloroacetophenone (11.7 g) in methanol (100 cc), and the mixture is left with stirring for 2 hours at the same temperature. The reaction mixture is evaporated to dryness at 50° C. under reduced pressure (20 mm Hg; 2.7 kPa). The residue obtained is dissolved in dichloromethane (50 cc), and the organic phase is dried over anhydrous magnesium sulphate, filtered and concentrated to dryness at 40° C. under reduced pressure (10 mm Hg; 2.7 kPa). α-Methylthio-4-chloroacetophenone (9.9 g) is thereby obtained, and is used in the crude state in the subsequent syntheses.

EXAMPLE 12

The procedure is as in Example 4, starting with ethyl 2-dimethylamino-6-(4-methylphenyl)-5-methylthio-6-oxo-2,4-hexadienoate (4.1 g) and 1N aqueous hydrochloric acid solution (18.5 cc) in ethanol (18.5 cc). The mixture is heated to boiling for 5 minutes, and then cooled to a temperature in the region of 20° C. After purification by recrystallization in boiling cyclohexane (35 cc), ethyl 2-hydroxy-6-(4-methylphenyl)-5-methylthio-6-oxo-2,4-hexadienoate (2.9 g), m.p. 78° C., is obtained.

Ethyl 2-dimethylamino-6-(4-methylphenyl)-5-methylthio-6-oxo-2,4-hexadienoate may be prepared in the following manner:

The procedure is as in Example 4 for the preparation of ethyl 6-phenyl-6-oxo-5-methylthio-2-dimethylamino-2,4-hexadienoate, starting with N-(3-dimethylamino-3-ethoxycarbonylpropenylidene)-N-methylmethanaminium tetrafluroborate (23.4 g), a 2M ethanolic solution of sodium ethylate (40.8 cc) and α-methylthio-4-methylacetophenone (14.7 g) in ethanol (163 cc). After purification on a silica column with a mixture of cyclohexane and ethyl acetate (50:50 by volume) as eluent, and recrystallization in boiling cyclohexane (65 cc), ethyl 2-dimethylamino-6-(4-methylphenyl)-5-methylthio-6-oxo-2,4-hexadienoate (5.9 g), m.p. 98° C., is obtained.

α-Methylthio-4-methylacetophenone may be prepared in the following manner:

The procedure is as in Example 4 for the preparation of α-methylthioacetophenone; sodium methanethiolate (6.8 g) is added in the course of 30 minutes at a temperature in the region of 20° C. to a stirred solution of α-bromo-4-methylacetophenone (20.8 g) in methanol (195 cc), and the mixture is left with stirring for 2 hours at the same temperature. α-Methylthio-4-methylacetophenone (16.5 g) is thereby obtained, and is used in the crude state in the subsequent syntheses.

EXAMPLE 13

The procedure is as in Example 4, starting with ethyl 2-dimethylamino-6-(4-methoxyphenyl)-5-methylthio-6-oxo-2,4-hexadienoate (6.1 g) and 1N aqueous hydrochloric acid solution (26.2 cc) in ethanol (26.2 cc). The mixture is heated to boiling for 5 minutes, and then cooled to a temperature in the region of 20° C. After purification by recrystallization in boiling isopropyl ether (35 cc), ethyl 2-hydroxy-6-(4-methoxyphenyl)-5-methylthio-6-oxo-2,4-hexadienoate (2.7 g), m.p. 88° C., is obtained.

Ethyl 2-dimethylamino-6-(4-methoxyphenyl)-5-methylthio-6-oxo-2,4-hexadienoate may be prepared in the following manner:

The procedure is as in Example 4 for the preparation of ethyl 6-phenyl-6-oxo-5-methylthio-2-dimethylamino-2,4-hexadienoate, starting with N-(3-dimethylamino-3-ethoxycarbonylpropenylidene)-N-methylmethanaminium tetrafluoroborate (13.9 g), a 2M ethanolic solution of sodium ethylate (24.2 cc) and α-methylthio-4-methoxyacetophenone (9.5 g) in ethanol (97 cc). After purification on a silica column with a mixture of cyclohexane and ethyl acetate (50:50 by volume) as eluent, ethyl 2-dimethylamino-6-(4-methoxyphenyl)-5-methylthio-6-oxo-2,4-hexadienoate (6.1 g) is obtained, and is used in the crude state in the subsequent syntheses.

α-Methylthio-4-methoxyacetophenone may be prepared in the following manner:

The procedure is as in Example 4 for the preparation of α-methylthioacetophenone, starting with a stirred solution of α-bromo-4-methoxyacetophenone (11.5 g) in methanol (100 cc); sodium methanethiolate (3.5 g) is added in the course of 15 minutes at a temperature in the region of 20° C., and the mixture is left with stirring for 12 hours at this temperature. α-Methylthio-4-methoxyacetophenone (9.5 g) is thereby obtained, and is used in the crude state in the subsequent syntheses.

EXAMPLE 14

The procedure is as in Example 4, starting with ethyl 2-dimethylamino-5-methylthio-6-oxo-6-(4-piperidinophenyl)-2,4-hexadienoate (23.5 g) and 1N hydrochloric acid (139 cc) in ethanol (139 cc). The mixture is stirred for 16 hours at a temperature in the region of 20° C. After purification by chromatrography on a silica column with dichloromethane as eluent and a second chromatography on a second silica column with a mixture of cyclohexane and ethyl acetate (50:50 by volume) as eluents; the corresponding eluate is concentrated to dryness at 40° C. under reduced pressure (20 mm Hg; 2.7 kPa). The residue is recrystallized in boiling isopropyl ether (100 cc). Ethyl 2-hydroxy-5-methylthio-6-oxo-6-(4-piperidinophenyl)-2,4-hexadienoate (3 g), m.p. 65° C., is thereby obtained.

Ethyl 2-dimethylamino-5-methylthio-6-oxo-6-(4-piperidinophenyl)-2,4-hexadienoate may be obtained in the following manner:

The procedure is as in Example 4 for the preparation of ethyl 6-phenyl-6-oxo-5-methylthio-2-dimethylamino-2,4-hexadienoate, starting with N-(3-dimethylamino-3-ethoxycarbonylpropenylidene)-N-methylmethanaminium tetrafluoroborate (34.4 g), a 2M ethanolic solution of sodium ethylate (60 cc) and α-methylthio-4-piperidinoacetophenone (30 g) in ethanol (300 cc). After purification by chromatography on a silica column with a mixture of cyclohexane and ethyl acetate (50:50 by volume) as eluent, and recrystallization in boiling isopropanol (150 cc), ethyl 2-dimethylamino-5-methylthio-6-oxo-6-(4-piperidinophenyl)-2,4-hexadienoate (27 g), m.p. 113° C., is obtained.

α-Methylthio-4-piperidinoacetophenone may be prepared in the following manner:

The procedure is as in Example 4 for the preparation of α-methylthioacetophenone. Sodium methanethiolate (20.1 g) is added in the course of 90 minutes at a temperature in the region of 20° C. to a stirred solution of α-chloro-4-piperidinoacetophenone (67 g) in methanol (670 cc), and stirring is continued for 3 hours at the same temperature. After purification by recrystallization in a boiling mixture (1,400 cc) of hexane and cyclohexane (90:10 by volume), α-methylthio-4-piperidinoacetophenone (55 g), m.p. 66° C., is obtained.

α-Chloro-4-piperidinoacetophenone may be prepared in the following manner:

Titanium III chloride (620 cc), in 15% strength aqueous solution, is added to a stirred solution of α,α'-dibromo-4-piperidinoacetophenone (124 g) in 12N aqueous hydrochloric acid solution (990 cc). The solution is heated to boiling for 2 hours 30 minutes, and then cooled to a temperature in the region of 20° C. The reaction mixture is alkalinized to pH 11 with 10N aqueous sodium hydroxide solution (900 cc), and then taken up with dichloromethane (750 cc) and filtered. The organic phase is separated off after settling has taken place, washed with water (2×200 cc), dried over sodium sulphate, filtered and evaporated to dryness at 40° C. under reduced pressure (20 mm Hg; 2.7 kPa). The residue is recrystallized in boiling isopropanol (400 cc). α-Chloro-4-piperidinoacetophenone (67 g), m.p. 125° C., is obtained.

α,α'-Dibromo-4-piperidinoacetophenone may be prepared in the following manner:

A mixture of bromine (50 cc) and hydrobromic acid (75 cc) is added in the course of 40 minutes at a temperature in the region of 20° C. to a stirred solution of 4- piperidinoacetophenone (99.5 g) in 8.6N aqueous hydrobromic acid solution (200 cc), the temperature being held at approximately 20° C. Stirring is maintained for 2 hours at the same temperature. The reaction mixture is filtered, and the cake washed with water (300 cc). The solid is ground and taken up with dichloromethane (800 cc). The solution obtained is alkalinized to pH 11 with 10N sodium hydroxide (200 cc) and taken up with water (600 cc). The organic phase is separated off after settling has taken place, dried over anhydrous magnesium sulphate, filtered and evaporated to dryness at 40° C. under reduced pressure (20 mm Hg; 2.7 kPa). The residue is recrystallized in boiling ethanol (2,160 cc). α,α'-Dibromo-4-piperidinoacetophenone (124 g), m.p. 134° C., is obtained.

EXAMPLE 15

The procedure is as in Example 5, starting with ethyl 5-cyano-2-dimethylamino-5-phenylthio-2,4-pentadienoate (12.5 g) and a 4N solution (51.7 cc) of hydrochloric acid in ethanol. The mixture is heated to boiling for 3 minutes, and then cooled to a temperature in the region of 20° C. After purification by recrystallization in boiling isopropyl ether (55 cc), ethyl 5-cyano-2-hydroxy-5-phenylthio-2,4-pentadienoate (3.2 g), m.p. 112° C., is obtained.

Ethyl 5-cyano-2-dimethylamino-5-phenylthio-2,4-pentadienoate may be prepared in the following manner:

The procedure is as in Example 2, starting with N-(3-dimethylamino-3-ethoxycarbonylpropenylidene)-N-methylmethanaminium tetrafluoroborate (97 g), a 2M ethanolic solution of sodium ethylate (170 cc) and phenylthioacetonitrile (50.5 g) in ethanol (700 cc). After purification by recrystallization in boiling isopropanol (250 cc), ethyl 2-dimethylamino-5-phenylthio-2,4-pentadienoate (21.4 g), m.p. 88° C., is obtained.

Phenylthioacetonitrile may be prepared in the following manner:

Chloroacetonitrile (11.4 cc) is added at a temperature in the region of 5° C., in the course of 45 minutes, to a stirred solution of thiophenol (20 g) and a 2M ethanolic solution of sodium ethylate (90 cc). Stirring is maintained for 5 hours at a temperature in the region of 20° C. The reaction mixture is filtered, and the filtrate is evaporated to dryness at 50° C. under vacuum (20 mm Hg; 2.7 kPa). The residue is dissolved in a mixture (30 cc) of cyclohexane and ethyl acetate (70:30 by volume) and the solution is poured onto silica (1,000 g) contained in a column 6.5 cm in diameter. Elution is performed with a mixture of cyclohexane and ethyl acetate (70:30 by volume) as eluent. Phenylthioacetonitrile (14.5 g) is obtained, and is used in the crude state in the subsequent phases.

EXAMPLE 16

The procedure is as in Example 2, starting with diethyl 5-(4-chlorophenylthio)-2-dimethylamino-2,4-hexadienedioate (10 g) and 1N aqueous hydrochloric acid solution (39 cc) in ethanol (39 cc). The mixture is heated to boiling for 2 minutes, and then cooled to a temperature in the region of 20° C. After purification by recrystallization in boiling cyclohexane (135 cc), diethyl 5-(4-chlorophenylthio)-2-hydroxy-2,4-hexadienedioate (6.8 g), m.p. 84° C., is obtained.

Diethyl 5-(4-chlorophenylthio)-2-dimethylamino-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (14.3 g), a 2M ethanolic solution of sodium ethylate (25 cc) and ethyl (4-chlorophenylthio)acetate (11.5 g) in ethanol (100 cc). Diethyl 5-(4-chlorophenylthio)-2-dimethylamino-2,4-hexadienedioate (19 g) is thereby obtained, and is used in the crude state in the subsequent phases.

Ethyl (4-chlorophenylthio)acetate may be prepared in the following manner:

The procedure is as in Example 2 for the preparation of ethyl (phenylthio)acetate starting with ethyl bromoacetate (16.7 g), a 2M ethanolic solution of sodium ethylate (50 cc) and 4-chlorothiophenol (14.5 g). Ethyl (4-chlorophenylthio)acetate (20.7 g) is thereby obtained, and is used in the crude state in the subsequent phases.

EXAMPLE 17

The procedure is as in Example 2, starting with diethyl 2-dimethylamino-5-(4-methoxyphenylthio)-2,4-hexadienedioate (10 g) and 1N aqueous hydrochloric acid solution (39.5 cc) in ethanol (39.5 cc). The mixture is heated to boiling for 3 minutes, and then cooled to a temperature in the region of 20° C. After purification by chromatography on a silica column with a mixture of cyclohexane and ethyl acetate (50:50 by volume) as eluent, and recrystallization in boiling cyclohexane (105 cc), diethyl 2-hydroxy-5-(4-methoxyphenylthio)-2,4-hexadienedioate (6 g), m.p. 88° C., is obtained.

Diethyl 2-dimethylamino-4-(4-methoxyphenylthio)-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (17.2 g), a 2M ethanolic solution of sodium ethylate (30 cc) and ethyl (4-methoxyphenylthio)acetate (13.6 g) in ethanol (136 cc). After purification by recrystallization in boiling isopropyl ether (110 cc), diethyl 2-dimethylamino-5-(4-methoxyphenylthio)-2,4-hexadienedioate (8.4 g), m.p. 78° C., is obtained.

Ethyl (4-methoxyphenylthio)acetate may be prepared in the following manner:

The procedure is as in Example 2 for the preparation of ethyl (phenylthio)acetate starting with ethyl bromoacetate (11.7 g), a 2M ethanolic solution of sodium ethylate (35 cc) and 4-methoxythiophenol (10 g). Ethyl (4-methoxyphenylthio)acetate (13.6 g) is thereby obtained, and is used in the crude state in the subsequent syntheses.

EXAMPLE 18

The procedure is as in Example 2, starting with diethyl 5-benzylthio-2-dimethylamino-2,4-hexadienedioate (10 g) and 1N aqueous hydrochloric acid solution (41.3 cc) in ethanol (41.3 cc). The mixture is heated to boiling for 2 minutes, and then cooled to a temperature in the region of 20° C. After purification by chromatography on a silica column with a mixture of cyclohexane and ethyl acetate (30:70 by volume) as eluent, diethyl 5-benzylthio-2-hydroxy-2,4-hexadienedioate (6.3 g) (m.p. <40° C.) is obtained [Rf=0.6; thin layer chromatography on silica gel; eluent: cyclohexane/ethyl acetate (30:70 by volume)].

Diethyl 5-benzylthio-2-dimethylamino-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (15.7 g), a 2M ethanolic solution of sodium ethylate (27.5 cc) and ethyl (benzylthio)acetate (11.6 g) in ethanol (110 cc). Diethyl 5-benzylthio-2-dimethylamino-2,4-hexadienedioate (19.2 g) is thereby obtained, and is used in the crude state in the subsequent phases.

Ethyl(benzylthio)acetate may be prepared in the following manner:

The procedure is as in Example 2 for the preparation of ethyl (phenylthio)acetate starting with ethyl bromoacetate (16.7 g), a 2M ethanolic solution of sodium ethylate (50 cc) and benzylmercaptan (11.7 cc). Ethyl (benzylthio)acetate (19.4 g) is thereby obtained, and is used in the crude state in the subsequent phases.

EXAMPLE 19

The procedure is as in Example 2, starting with diethyl 5-allylthio-2-dimethylamino-2,4-hexadienedioate (5.1 g) and 1N aqueous hydrochloric acid solution (24.4 cc) in ethanol (24.4 cc). The mixture is heated to boiling for 3 minutes, and then cooled to a temperature in the region of 20° C. After purification by chromatography on a silica column with a mixture of cyclohexane and ethyl acetate (75:25 by volume) as eluent, diethyl 5-allylthio-2-hydroxy-2,4-hexadienedioate (2.3 g) is obtained in the form of a yellow oil [Rf=0.2; thin layer chromatography on silica gel; eluent: cyclohexane/ethyl acetate (75:25 by volume)].

Diethyl 5-allylthio-2-dimethylamino-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (5.5 g), a 2M ethanolic solution of sodium ethylate (9.7 cc) and ethyl (allylthio)acetate (3.1 g) in ethanol (31 cc). Diethyl 5-allylthio-2-dimethylamino-2,4-hexadienedioate (5.1 g) is thereby obtained, and is used in the crude state in the subsequent phases.

Ethyl (allylthio)acetate may be prepared in the following manner:

The procedure is as in Example 2 for the preparation of ethyl phenylthioacetate, starting with ethyl bromoacetate (16.7 g), a 2M ethanolic solution of sodium ethylate (50 cc) and allylmercaptan (7.7 cc). After purification by chromatography on a silica column with cyclohexane as eluent, ethyl (allylthio)acetate (3.1 g) is obtained, and is used in the crude state in the subsequent phases.

EXAMPLE 20

The procedure is as in Example 2, starting with ethyl 2-dimethylamino-5-ethoxycarbonyl-2,4-tridecadienoate (9.3 g) and 1N aqueous hydrochloric acid solution (40 cc) in ethanol (40 cc). The mixture is heated to boiling for 5 minutes, and then cooled to a temperature in the region of 20° C. After purification by recrystallization in 40°-65° petroleum ether (100 cc), ethyl 5-ethoxycarbonyl-2-hydroxy-2,4-tridecadienoate (3.9 g), m.p. 58° C., is obtained.

Ethyl 2-dimethylamino-5-ethoxycarbonyl-2,4-tridecadienoate may be prepared in the following manner:

Ethyl n-decanoate (10 g) is added in the course of 10 minutes at a temperature in the region of −78° C. to a stirred mixture of diisopropylamine (5.6 cc), a 1.6M solution (37.5 cc) of n-butyllithium in hexane and tetrahydrofuran (30 cc). Stirring is maintained for 30 minutes at the same temperature, N-(3-dimethylamino-3-ethoxycarbonylpropenylidene)-N-methylmethanaminium tetrafluoroborate (14.3 g) is then added and stirring is maintained for 3 hours at a temperature in the region of −78° C. After a gradual warming to approximately 20° C., ammonium chloride (4 g) dissolved in water (50 cc) is added to the reaction medium. Dichloromethane (200 cc) and water (100 cc) are added, and the organic phase is separated off after settling has taken place. The aqueous phase is washed with dichloromethane (2×50 cc). The organic phases are combined, dried over anhydrous magnesium sulphate, filtered and evaporated at 40° C. under reduced pressure (20 mm Hg; 2.7 kPa). The residue is dissolved in a mixture (30 cc) of cyclohexane and ethyl acetate (60:40 by volume), and the solution obtained is poured onto silica (600 g) contained in a column 7 cm in diameter. Elution is performed with a mixture of cyclohexane and ethyl acetate (60:40 by volume), and the eluate is concentrated to dryness at 40° C. under reduced pressure (20 mm Hg; 2.7 kPa). Ethyl 2-dimethylamino-5-ethoxycarbonyl-2,4-tridecadienoate (9.8 g) is thereby obtained, and is used in the crude state in the subsequent syntheses.

Ethyl n-decanoate may be prepared in the following manner:

n-Decanoic acid (17.2 g), 36N aqueous sulphuric acid solution (3 cc) and ethanol (300 cc) are heated to boiling for 4 hours. After being cooled to a temperature in the region of 20° C., the solution is concentrated to dryness at 50° C. under vacuum (20 mm Hg; 2.7 kPa), and the residue is then taken up with dichloromethane (200 cc). The organic phase is washed with saturated aqueous sodium bicarbonate solution (2×100 cc), separated off after settling has taken place, dried over anhydrous magnesium sulphate, filtered and concentrated to dryness at 40° C. under reduced pressure (20 mm Hg; 2.7 kPa). Ethyl n-decanoate (18 g) is thereby obtained, and is used in the crude state in the subsequent syntheses.

EXAMPLE 21

The procedure is as in Example 2, starting with ethyl 5-dimethylamino-2-phenylthio-2,4-pentadienoate (5 g) and 1N aqueous hydrochloric acid solution (108 cc) in ethanol (90 cc). The mixture is heated to boiling for 2 minutes, and then cooled to a temperature in the region of 20° C. After purification by recrystallization in a boiling mixture (15 cc) of cyclohexane and ethyl acetate (50:50 by volume), ethyl 5-hydroxy-2-phenylthio-2,4-pentadienoate (1.5 g), m.p. 120° C., is obtained.

Ethyl 5-dimethylamino-2-phenylthio-2,4-pentadienoate may be prepared in the following manner:

A 2M ethanolic solution of sodium ethylate (64 cc) is added at a temperature in the region of 20° C., in the course of 15 minutes, to a stirred solution, maintained under a nitrogen atmosphere, of ethyl (phenylthio)acetate (25.1 g) in ethanol (280 cc). Stirring is maintained for 30 minutes at the same temperature, and N-(3-dimethylaminopropenylidene)-N-methylmethanaminium chloride (20.8 g) is then added. The reaction medium is stirred for 15 hours at a temperature in the region of 20°

C. The mixture is concentrated to dryness at 40° C. under reduced pressure (20 mm Hg; 2.7 kPa), and then taken up with water (200 cc). The precipitate formed is filtered off, washed with water (50 cc) and recrystallized in boiling ethanol (125 cc). Ethyl 5-dimethylamino-2-phenylthio-2,4-pentadienoate (18.1 g), m.p. 128° C., is obtained.

N-(3-Dimethylaminopropenylidene)-N-methylmethanaminium chloride may be prepared according to the method described by V. NAIR and C. S. COOPER, J. Org. Chem., 46, 4759 (1981).

EXAMPLE 22

Acetyl chloride (1.2 cc) is added at a temperature of approximately 20° C., and in the course of 5 minutes, to a stirred solution, through which a stream of nitrogen is passed, of diethyl 2-hydroxy-5-phenylthio-2,4-hexadienedioate (5 g) and triethylamine (2.4 cc) in tetrahydrofuran (45 cc). Stirring is maintained for 2 hours at the same temperature. The mixture is taken up with water (100 cc) and dichloromethane (100 cc). The organic phase is separated off after settling has taken place, and the aqueous phase is extracted with dichloromethane (2×50 cc). The organic phases are combined, dried over anhydrous magnesium sulphate, filtered and concentrated to dryness at 40° C. under reduced pressure (20 mm Hg; 2.7 kPa). The oil obtained is dissolved in a mixture (10 cc) of cyclohexane and ethyl acetate (70:30 by volume), and poured onto silica (300 g) contained in a column 4 cm in diameter. Elution is performed with a mixture of cyclohexane and ethyl acetate (70:30 by volume), and the corresponding eluate is concentrated to dryness at 40° C. under reduced pressure (20 mm Hg; 2.7 kPa). Diethyl 2-acetoxy-5-phenylthio-2,4-hexadienedioate (4.5 g) is obtained in the form of an orange-coloured oil [Rf=0.50; thin layer chromatography on silica gel; eluent: cyclohexane/ethyl acetate (70:30 by volume)].

EXAMPLE 23

The procedure is as in Example 2, starting with 1-ethyl 6-cyclohexyl 2-dimethylamino-5-phenylthio-2,4-hexadienedioate (4.5 g) and 12N aqueous hydrochloric acid solution (0.5 cc) in tetrahydrofuran (50 cc). The solution is stirred for 15 hours at a temperature of approximately 20° C. After purification by recrystallization in boiling cyclohexane (70 cc), 1-ethyl 6-cyclohexyl 2-hydroxy-5-phenylthio-2,4-hexadienedioate (2.3 g), m.p. 110° C., is obtained.

1-Ethyl 6-cyclohexyl 2-dimethylamino-5-phenylthio-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (13.7 g), a 1.6M solution (33.1 cc) of n-butyllithium in hexane and cyclohexyl (phenylthio)acetate (12 g) in tetrahydrofuran (150 cc). After purification by chromatography on a silica column with a mixture of cyclohexane and ethyl acetae (80:20 by volume) as eluent, 1-ethyl 6-cyclohexyl 2-dimethylamino-5-phenylthio-2,4-hexadienedioate (9.7 g) is obtained, and is used in the crude state in the subsequent phases.

Cyclohexyl (phenylthio)acetate may be prepared in the following manner:

The procedure is as in Example 20 for the preparation of ethyl n-decanoate, starting with (phenylthio)acetic acid (20 g) and 36N aqueous sulphuric acid solution (0.32 cc) in cyclohexanol (100 cc). After purification by chromatography on a silica column with a mixture of cyclohexane and ethyl acetate (70:30 by volume) as eluent, cyclohexyl (phenylthio)acetate (29 g) is obtained, and is used in the crude state in the subsequent phases.

EXAMPLE 24

The procedure is as in Example 2, starting with ethyl 5-dimethylamino-5-phenyl-2-phenylthio-2,4-pentadienoate (3.5 g) and 1N aqueous hydrochloric acid solution (17 cc) in ethanol (17 cc). The solution is heated to boiling for 2 minutes, and then cooled to a temperature in the region of 20° C. After purification by chromatography on a silica column with dichloromethane as eluent, ethyl 5-oxo-5-phenyl-2-phenylthio-2-pentenoate (1.7 g) is obtained in the form of a yellow oil (Rf=0.40; thin layer chromatography on silica gel; eluent: dichloromethane).

Ethyl 5-dimethylamino-5-phenyl-2-phenylthio-2,4-pentadienoate may be prepared in the following manner:

The procedure is as in Example 2 for the preparation of diethyl 2-dimethylamino-5-phenylthio-2,4-hexadienedioate, starting with N-(3-dimethylamino-3-phenylpropenylidene)-N-methylmethanaminium tetrafluoroborate (15.4 g), a 2M solution of sodium ethylate (26.5 cc) and ethyl (phenylthio)acetate (10.4 g) in ethanol (150 cc). After purification by chromatography on a silica column with dichloromethane as eluent, ethyl 5-dimethylamino-5-phenyl-2-phenylthio-2,4-pentadienoate (9.7 g), m.p. 99° C., is obtained.

N-(3-Dimethylamino-3-phenylpropenylidene)-N-methylmethanaminium tetrafluoroborate may be prepared in the following manner:

The procedure is as in Example 2 for the preparation of N-(3-ethoxy-3-ethoxycarbonylpropenylidene)-N-methylmethanaminium tetrafluoroborate and N-(3-dimethylamino-3-ethoxycarbonylpropenylidene)-N-methylmethanaminium tetrafluoroborate, starting with 3-dimethylamino-1-phenyl-2-propene-1-one, triethyloxonium tetrafluoroborate (12.3 g) and dimethylamine (5 cc) in dichloromethane (50 cc). After purification by recrystallization in boiling isopropanol (100 cc), N-(3-dimethylamino-3-phenylpropenylidene)-N-methylmethanaminium tetrafluoroborate (15.4 g), m.p. 136° C., is obtained.

3-dimethylamino-1-phenyl-2-propene-1 one may be prepared according to the method described by H. BRADERECK, F. EFFARBERGER and H. BOTSCH, Chem. Ber. 97, 3397 (1964).

EXAMPLE 25

The procedure is as in Example 2, starting with diethyl 2-dimethylamino-5-phenyl-2,4-hexadienedioate (4.6 g) and 1N aqueous hydrochloric acid solution (28 cc) in ethanol (28 cc). The solution is stirred at a temperature in the region of 20° C. for 15 hours. After purification by recrystallization in boiling cyclohexane (35 cc), diethyl 2-hydroxy-5-phenyl-2,4-hexadienedioate (1.8 g), m.p. 107° C., is obtained.

Diethyl 2-dimethylamino-5-phenyl-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (10 g), a 2M ethanolic solution of sodium ethylate (21 cc) and ethyl phenylacetate (5.6 cc) in ethanol (100 cc). After purification by chromatography on a silica column, with a mixture of cyclohexane and ethyl acetate (80:20 by volume) as eluent, diethyl 2-dimethylamino-5-phenyl-2,4-hexadienedioate (4.6 g) is obtained, and is used in the crude state in the subsequent phases.

EXAMPLE 26

The procedure is as in Example 4, starting with ethyl 2-dimethylamino-6-(3,4-isopropylenedioxyphenyl)-5-methylthio-6-oxo-2,4-hexadienoate (4.9 g) and 1N aqueous hydrochloric acid solution (20 cc) in ethanol (20 cc). The mixture is heated to boiling for 5 minutes, and then cooled to a temperature in the region of 20° C. After purification by recrystallization in boiling isopropyl ether (70 cc), ethyl 2-hydroxy-6-(3,4-isopropylenedioxyphenyl)-5-methylthio-6-oxo-2,4-hexadienoate (1.1 g), m.p. 134° C., is obtained.

Ethyl 2-dimethylamino-6-(3,4-isopropylenedioxyphenyl)-5-methylthio-6-oxo-2,4-hexadienoate may be prepared in the following manner:

The procedure is as in Example 4 for the preparation of ethyl 6-phenyl-6-oxo-5-methylthio-2-dimethylamino-2,4-hexadienoate, starting with N-(3-dimethylamino-3-ethoxycarbonylpropenylidene)-N-methylmethanaminium tetrafluoroborate (7.2 g), a 2M ethanolic solution of sodium ethylate (12.5 cc) and 2,2-dimethyl-5-[2-(methylthio)acetyl]-1,3-benzodioxole (6 g) in ethanol (50 cc). After purification on a silica column with a mixture of cyclohexane and ethyl acetate (50:50 by volume) as eluent, ethyl 2-dimethylamino-6-(3,4-isopropylenedioxyphenyl)-5-methylthio-6-oxo-2,4-hexadienoate (3.9 g) is obtained, and is used in the crude state in subsequent syntheses.

2,2-Dimethyl-5-[2-(methylthio)acetyl]-1,3-benzodioxole may be prepared in the following manner:

The procedure is as in Example 4 for the preparation of α-methylthioacetophenone, starting with a stirred solution of 5-(2-bromoacetyl)-2,2-dimethyl-1,3-benzodioxole (14.9 g) in methanol (150 cc). Sodium methanethiolate (3.8 g) is added in the course of 5 minutes at a temperature in the region of 20° C., and the mixture is left with stirring for 15 hours at the same temperature. 2,2-Dimethyl-5-[2-(methylthio)acetyl]-1,3-benzodioxole (11 g) is thereby obtained, and is used in the crude state in the subsequent syntheses.

5-(2-Bromoacetyl)-2,2-dimethyl-1,3-benzodioxole may be prepared in the following manner:

Bromine (1.5 cc) is added in the course of 5 minutes at a temperature in the region of 20° C. to a stirred solution of 5-acetyl-2,2-dimethyl-1,3-benzodioxole (5.8 g) in carbon tetrachloride (100 cc), and the mixture is left with stirring for 15 hours at the same temperature. The reaction mixture is taken up with water (150 cc). The organic phase is separated off after settling has taken place, dried over anhydrous magnesium sulphate, filtered and evaporated to dryness at 40° C. under reduced pressure (20 mm Hg; 2.7 kPa). 5-(2-Bromoacetyl)-2,2-dimethyl-1,3-benzodioxole (7.1 g) is obtained, and is used in the crude state in the subsequent syntheses.

5-Acetyl-2,2-dimethyl-1,3-benzodioxole may be prepared according to the method described by G. BENOIT and B. MILLET, Bull. Soc. Chim. Fr. 1960, 638.

EXAMPLE 27

The procedure is as in Example 4, starting with ethyl 6-(3,4-dihydroxyphenyl)-2-dimethylamino-5-methylthio-6-oxo-2,4-hexadienoate (1.9 g) and 1N aqueous hydrochloric acid solution (10.8 cc) in ethanol (10.8 cc). The mixture is heated to boiling for 5 minutes, and then cooled to a temperature in the region of 20° C. After purification by crystallization in isopropyl ether (100 cc), ethyl 6-(3,4-dihydroxyphenyl)-2-hydroxy-5-methylthio-6-oxo-2,4-hexadienoate (0.6 g), m.p. 156° C., is obtained.

Ethyl 6-(3,4-dihydroxyphenyl)-2-dimethylamino-5-methylthio-6-oxo-2,4-hexadienoate may be prepared in the following manner:

The procedure is as in Example 4 for the preparation of ethyl 6-phenyl-6-oxo-5-methylthio-2-dimethylamino-2,4-hexadienoate, starting with N-(3-dimethylamino-3-ethoxycarbonylpropenylidene)-N-methylmethanaminium tetrafluoroborate (11.4 g), a 2M ethanolic solution of sodium ethylate (60 cc) and 4-[2-(methylthio)acetyl]pyrocatechol (7.9 g) in ethanol (60 cc). After purification on a silica column with a mixture of cyclohexane and ethyl acetate (50:50 by volume) as eluent, ethyl 6-(3,4-dihydroxyphenyl)-2-dimethylamino-5-methylthio-6-oxo-2,4-hexadienoate (2.4 g), m.p. 144° C., is obtained.

4-[2-(Methylthio)acetyl]pyrocatechol may be prepared in the following manner:

The procedure is as in Example 4 for the preparation of α-methylthioacetophenone, starting with a stirred solution of 4-(2-chloroacetyl)pyrocatechol (18.6 g) in methanol (200 cc). Sodium methanethiolate (7 g) is added in the course of 15 minutes at a temperature in the region of 20° C., and the mixture is left with stirring for 3 hours at the same temperature. 4-[2-(Methylthio)acetyl]pyrocatechol (14.5 g), m.p. 107° C., is thereby obtained.

EXAMPLE 28

The procedure is as in Example 4, starting with ethyl 2-dimethylamino-5-methoxy-6oxo-6-phenyl-2,4-hexadienoate (8 g) and 1N aqueous hydrochloric acid solution (40 cc) in ethanol (40 cc). The mixture is heated to boiling for 5 minutes, and then cooled to a temperature in the region of 20° C. After purification by chromatography on a silica column with a mixture of cyclohexane and ethyl acetate (50:50 by volume) as eluent, and recrystallization in boiling isopropyl ether (70 cc), ethyl 2-hydroxy-5-methoxy-6-oxo-6-phenyl-2,4-hexadienoate (4 g), m.p. 84° C., is obtained.

Ethyl 2-dimethylamino-5-methoxy-6-oxo-6-phenyl2,4-hexadienoate may be prepared in the following manner:

The procedure is as in Example 4 for the preparation of ethyl 6-phenyl-6-oxo-5-methylthio-2-dimethylamino2,4-hexadienoate, starting with N-(3-dimethylamino-3-ethoxycarbonylpropenylidene)-N-methylmethanaminium tetrafluoroborate (11.4 g), a 2M ethanolic solution of sodium ethylate (20 cc) and α-methoxyacetophenone (6 g) in ethanol (50 cc). After purification by chromatography on a silica column with a mixture of dicholoromethane and ethyl acetate (50:50 by volume) as eluent, ethyl 2-dimethylamino-5-methoxy-6-oxo-6-phenyl-2,4-hexadienoate (8.1 g) is obtained, and is used in the crude state in the subsequent syntheses.

α-Methoxyacetophenone is prepared according to R. B. MOFFET and R. L. SCHRINER, Org. Synth. 3, 562 (1955).

EXAMPLE 29

The procedure is as in Example 2, starting with diethyl 2-dimethylamino-5-(4-methylbenzylthio)-2,4-hexadienedioate (5 g), 12N aqueous hydrochloric acid solution (20 cc) and ethanol (20 cc). The mixture is heated to boiling for 1 minute, and is then cooled to a temperature of approximately 20° C. After purification by recrystallization in boiling petroleum ether (40°–60° C., 84 cc), diethyl 2-hydroxy-5-(4-methylbenzylthio)-2,4-hexadienedioate (3.2 g), m.p. 66° C., is obtained.

Diethyl 2-dimethylamino-5-(4-methylbenzylthio)2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (5.7 g), a 2M ethanolic solution of sodium ethylate (10 cc) and ethyl (4-methylbenzylthio)acetate (4.5 g) in ethanol (50 cc). After purification by chromatography on a silica column with a mixture of cyclohexane and ethyl acetate (50:50 by volume) as eluent, diethyl 2-dimethylamino-5-(4-methylbenzylthio)-2,4-hexadienedioate (5 g) is obtained in the form of a yellow oil, and is used in the crude state in the subsequent syntheses.

Ethyl (4-methylbenzylthio)acetate may be prepared in the following manner:

Ethyl 2-mercaptoacetate (8.5 cc) is added in the course of 15 minutes at a temperature in the region of 20° C. to a stirred solution, through which a stream of nitrogen is passed, of a 2M ethanolic solution of sodium ethylate (37.5 cc) and ethanol (50 cc). The mixture is left with stirring for 15 minutes at the same temperature, and α-bromo-p-xylene (13.9 g) is then added in the course of 20 minutes at a temperature in the region of 20° C. Stirring is maintained for 60 minutes at this temperature, and the reaction mixture is then evaporated to dryness at 50° C. under reduced pressure (20 mm Hg; 2.7 kPa). The residue obtained is dissolved in dichloromethane (100 cc), and the organic phase is dried over anhydrous magnesium sulphate, filtered and concentrated to dryness at 40° C. under reduced pressure (20 mm Hg; 2.7 kPa). Ethyl (4-methylbenzylthio)acetate (15.6 g) is thereby obtained, and is used in the crude state in the subsequent syntheses.

EXAMPLE 30

The procedure is as in Example 2, starting with diethyl 2-dimethylamino-5-(4-phenylbenzylthio)-2,4-hexadienedioate (6 g), 12N aqueous hydrochloric acid solution (20.5 cc) and ethanol (40 cc). The mixture is heated to boiling for 1 minute, and is then cooled to a temperature of approximately 20° C. After purification by recrystallization in boiling isopropanol (70 cc), diethyl 2-hydroxy-5-(4-phenylbenzylthio)-2,4-hexadienedioate (4.25 g), m.p. 133° C., is obtained.

Diethyl 2-dimethylamino-5-(4-phenylbenzylthio)2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (5.7 g), a 2M ethanolic solution of sodium ethylate (10 cc) and ethyl (4-phenylbenzylthio)acetate (5.7 g) in ethanol (50 cc). After purification by chromatography on a silica column with a mixture of cyclohexane and ethyl acetate (70:30 by volume) as eluent, diethyl 2-dimethylamino-5-(4-phenylbenzylthio)-2,4-hexadienedioate (6 g) is obtained in the form of a yellow oil, and is used in the crude state in the subsequent syntheses.

Ethyl (4-phenylbenzylthio)acetate may be prepared in the following manner:

The procedure is as in Example 29 for the preparation of ethyl (4-methylbenzylthio)acetate, starting with 4-chloromethylbiphenyl (10.25 g), a 2M ethanolic solution of sodium ethylate (25 cc) and ethyl 2-mercaptoacetate (6.1 g) in ethanol (150 cc). Ethyl (4-phenylbenzylthio)acetate (13.1 g) is thereby obtained, and is used in the crude state in the subsequent syntheses.

EXAMPLE 31

The procedure is as in Example 2, starting with diethyl 2-dimethylamino-5-(3-phenoxybenzylthio)-2,4-hexadienedioate (7 g), 12N aqueous hydrochloric acid solution (23 cc) and ethanol (46 cc). The mixture is heated to boiling for 1 minute, and is then cooled to a temperature of approximately 20° C. After purification by chromatography on a silica column with dichloromethane as eluent, diethyl 2-hydroxy-5-(3-phenoxybenzylthio)-2,4-hexadienedioate (4.5 g) is obtained in the form of a yellow oil (Rf=0.2; thin layer chromatography on silica gel; eluent: dichloromethane).

Diethyl 2-dimethylamino-5-(3-phenoxybenzylthio)2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetraflouroborate (5.7 g), a 2M ethanolic solution of sodium ethylate (10 cc) and ethyl (3-phenoxybenzylthio)acetate (6.1 g) in ethanol (50 cc). After purification by chromatography on a silica column with a mixture of cyclohexane and ethyl acetate (50:50 by volume) as eluent, diethyl 2-dimethylamino-5-(3-phenoxybenzylthio)-2,4-hexadienedioate (7 g) is obtained in the form of a yellow oil, and is used in the crude state in the subsequent syntheses.

Ethyl (3-phenoxybenzylthio)acetate may be prepared in the following manner:

The procedure is as in Example 29 for the preparation of ethyl (4-methylbenzylthio)acetate, starting with 1-chloromethyl-4-phenoxybenzene (21.5 g), a 2M ethanolic solution of sodium ethylate (50 cc) and ethyl 2-mercaptoacetate (12.2 g) in ethanol (200 cc). Ethyl (3-phenoxybenzylthio)acetate (28.8 g) is thereby obtained, and is used in the crude state in the subsequent syntheses.

EXAMPLE 32

The procedure is as in Example 4, starting with ethyl 2-dimethylamino-5-methylthio-6-(2-naphthyl)-6-oxo-2,4-hexadienoate (6.9 g), 12N aqueous hydrochloric acid solution (29 cc) and ethanol (29 cc). The mixture is heated to boiling for 5 minutes, and is then cooled to a temperature of approximately 20° C. After purification by recrystallization in boiling diisopropyl ether (300 cc), ethyl 2-hydroxy-5-methylthio-6-(2-naphthyl)-6-oxo-2,4-hexadienoate (2.7 g), m.p. 117° C., is obtained Ethyl 2-dimethylamino-5-methylthio-6-(2-naphthyl)6-oxo-2,4-hexadienoate may be prepared in the following manner:

The procedure is as in Example 4 for the preparation of ethyl 6-phenyl-6-oxo-5-methylthio-2-dimethylamino-2,4-hexadienoate, starting with N-(3-dimethylamino-3-ethoxycarbonylpropenylidene)-N-methylmethanaminium tetrafluoroborate (10.6 g), a 2M ethanolic solution of sodium ethylate (18.5 cc) and 2-[2-(methylthio)acetyl]naphthalene (8 g) in ethanol (50 cc). After purification by chromatography on a silica column with a mixture of cyclohexane and ethyl acetate (50:50 by volume) as eluent, ethyl 2-dimethylamino-5-methylthio-6-(2-naphthyl)-6-oxo-2,4-hexadienoate (5 g) is obtained in the form of an orange-coloured oil, and is used in the crude state in the subsequent syntheses.

2-[2-(Methylthio)acetyl]naphthalene may be prepared in the following manner:

The procedure is as in Example 4 for the preparation of α-methylthioacetophenone, starting with 2-(2-bromoacetyl)naphthalene (12.5 g) and sodium methanethiolate (3.5 g) in ethanol (100 cc). 2-[2-(Methylthio)acetyl]naphthalene (8 g) is thereby obtained, and is used in the crude state in the subsequent syntheses.

EXAMPLE 33

The procedure is as in Example 4, starting with diethyl 2-dimethylamino-5-(3-phenoxyphenyl)-2,4-hexadeinedioate, 12N aqueous hydrochloric acid solution (13 cc) and ethanol (13 cc). The mixutre is heated to boiling for 5 minutes, and is then cooled to a temperature of approximately 20° C. After purification by recrystallization in boiling diisopropylether (100 cc), diethyl 2-hydroxy-5-(3-phenoxyphenyl)-2,4-hexadienedioate (2.7 g), m.p. 108° C., is obtained.

Diethyl 2-dimethylamino-5-(3-phenoxyphenyl)-2,4-hexadienedioate may be prepared in the following manner:

The procedure is as in Example 4 for the preparation of ethyl 6-phenyl-6-oxo-5-methylthio-2-dimethylamino-2,4-hexadienoate, starting with N-(3-dimethylamino-3-ethoxycarbonylpropenylidene)-N-methylmethanaminium tetrafluoroborate (7.6 g), a 2M ethanolic solution of sodium ethylate (13.3 cc) and ethyl (3-phenoxyphenyl)acetate (6.8 g) in ethanol (70 cc). After purification by chromatography on a silica column with a mixture of cyclohexane and ethyl acetate (50:50 by volume) as eluent, diethyl 2-dimethylamino-5-(3-phenoxyphenyl)-2,4-hexadienoate (3.4 g) is obtained in the form of a yellow oil, and is used in the crude state in the subsequent syntheses.

Ethyl (3-phenoxyphenyl)acetate may be prepared in the following manner:

(3-Phenoxyphenyl)acetic acid (11.5 g) and 36N aqueous sulphuric acid solution (3 cc) in ethanol (200 cc) are brought to boiling for 72 hours. After being cooled to approximately 20° C., the reaction mixture is concentrated to dryness at 50° C. under reduced pressure (20 mm Hg; 2.7 kPa). The oil is dissolved in dichloromethane (300 cc); the organic phase is washed with water (150 cc), dried over anhydrous magnesium sulphate, filtered and concentrated to dryness at 40° C. under reduced pressure (20 mm Hg; 2.7 kPa). The residue is dissolved in a mixture (20 cc) of cyclohexane and ethyl acetate (50:50 by volume), and the solution is poured onto silica (400 g) contained in a column 5 cm in diameter. Elution is performed with a mixture of cyclohexane and ethyl acetate (50:50 by volume), and the corresponding eluate is concentrated to dryness at 40° C. under reduced pressure (20 mm Hg; 2.7 kPa). Ethyl (3-phenoxyphenyl)acetate (7.4 g) is thereby obtained, and is used in the crude state in the subsequent syntheses.

(3-Phenoxyphenyl)acetic acid may be prepared according to the method descrbied by D. Matthies et al., Arch. Pharm. 604 (1983).

EXAMPLE 34

The procedure is as in Example 2, starting with diethyl 2-dimethylamino-5-(4-trifluoromethylbenzylthio)-2,4-hexadienedioate (7.3 g), 12N aqueous hydrochloric acid solution (25.5 cc) and ethanol (50 cc). The mixture is heated to boiling for 1 minute, and is then cooled to a temperature of approximately 20° C. After purification by recrystallization in boiling petroleum ether (40°–60° C., 60 cc) diethyl 2-hydroxy-5-(4-trifluoromethylbenzylthio)-2,4-hexadienedioate (4.2 g), m.p. 73° C., is obtained.

Diethyl 2-dimethylamino-5-(4-trifluoromethylbenzylthio)-2,4-hexadienedioate may be prepared in the following manner:

The procedure is as in Example 2, for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (5.7 g), a 2M ethanolic solution of sodium ethylate (50 cc) and ethyl (4-trifluoromethylbenzylthio)acetate (5.6 g) in ethanol (50 cc). Diethyl 2-dimethylamino-5-(4-trifluoromethylbenzylthio)-2,4-hexadienedioate (7.3 g) is thereby obtained in the form of a yellow oil, and is used in the crude state in the subsequent syntheses.

Ethyl (4-trifluoromethylbenzylthio)acetate may be prepared in the following manner:

The procedure is as in Example 29 for the preparation of ethyl (4-methylbenzylthio)acetate, starting with 1-chloromethyl-4-trifluoromethylbenzene (9.8 g), a 2M ethanolic solution of sodium ethylate (25 cc) and ethyl 2-mercaptoacetate (6.1 g) in ethanol (120 cc). Ethyl (4-trifluoromethylbenzylthio)acetate (12.2 g) is thereby obtained, and is used in the crude state in the subsequent syntheses.

EXAMPLE 35

The procedure is as in Example 4, starting with ethyl 2-dimethylamino-6-(4-fluorophenyl)-5-methylthio-6-oxo-2,4-hexadienoate (9 g), 12N aqueous hydrochloric acid solution (36 cc) and ethanol (100 cc). The mixture is heated to boiling for 5 minutes, and is then cooled to a temperature of approximately 20° C. After purification by recrystallization in boiling cyclohexane (50 cc), ethyl 6-(4-fluorophenyl)-2-hydroxy-5-methylthio-6-oxo-2,4-hexadienoate (3.2 g), m.p. 95° C., is obtained.

Ethyl 2-dimethylamino-6-(4-fluorophenyl)-5-methylthio-6-oxo-2,4-hexadienoate may be prepared in the following manner:

The procedure is as in Example 4 for the preparation of ethyl 6-phenyl-6-oxo-5-methylthio-2-dimethylamino2,4-hexadienoate, starting with N-(3-dimethylamino-3-ethoxycarbonylpropenylidene)-N-methylmethanaminium tetrafluoroborate (10 g), a 2M ethanolic solution of sodium ethylate (21 cc) and α-methylthio-4-fluoroacetophenone (6.5 g) in ethanol (100 cc). After purification by chromatography on a silica column with a mixture of cyclohexane and ethyl acetate (50:50 by volume) as eluent, ethyl 2-dimethylamino-6-

(4-fluorophenyl)-5-methylthio-6-oxo-2,4-hexadienoate (9 g) is obtained in the form of an orange-coloured oil, and is used in the crude state in the subsequent syntheses.

α-Methylthio-4-fluoroacetophenone may be prepared in the following manner:

The procedure is as in Example 4 for the preparation of α-methylthioacetophenone, starting with α-bromo-p-fluoroacetophenone (25 g) and sodium methanethiolate (10.3 g) in ethanol (130 cc). After purification by chromatography on a silica column with a mixture of cyclohexane and ethyl acetate (50:50 by volume) as eluent, α-methylthio-4-fluoroacetophenone (21.9 g) is obtained, and is used in the crude state in the subsequent syntheses.

EXAMPLE 36

The procedure is as in Example 4, starting with ethyl 2-dimethylamino-6-(4bromophenyl)-5-methylthio-6-oxo-2,4-hexadienoate (7.7 g), 12N aqueous hydrochloric acid solution (25 cc) and ethanol (80 cc). The mixture is heated to boiling for 5 minutes, and is then cooled to a temperature of approximately 20° C. After purification by chromatography on a silica column with a mixture of cyclohexane and ethyl acetate (80:20 and then 50:50, by volume) as eluent, and recrystallization in boiling cyclohexane (40 cc), ethyl 6-(4-bromophenyl)-2-hydroxy-5-methylthio-6-oxo-2,4-hexadienoate (2.5 g), m.p. 84° C., is obtained.

Ethyl 2-dimethylamino-6-(4-bromophenyl)-5-methylthio-6-oxo-2,4-hexadienoate may be prepared in the following manner:

The procedure is as in Example 4 for the preparation of ethyl 6-phenyl-6-oxo-5-methylthio-2-dimethylamino-2,4-hexadienoate, starting with N-(3-dimethylamino-3-ethoxycarbonylpropenylidene)-N-methylmethanaminium tetrafluoroborate (10 g), a 2M ethanolic solution of sodium ethylate (21 cc) and α-methylthio-4-bromoacetophenone (8.6 g) in ethanol (100 cc). After purification by recrystallization in cyclohexane (100 cc), ethyl 2-dimethylamino-6-(4-bromophenyl)-5-methylthio-6-oxo-2,4-hexadienoate (7.7 g), m.p. 107° C., is obtained.

α-Methylthio-4-bromoacetophenone may be prepared in the following manner:

The procedure is as in Example 4 for the preparation of α-methylthioacetophenone, starting with α-p-dibromo acetophenone (30 g) and sodium methanethiolate (7.6 g) in ethanol (100 cc). After purification by chromatography on a silica column with a mixture of cyclohexane and dichloromethane (50:50 by volume) as eluent, α-methylthio-4-bromoacetophenone (22.4 g) is obtained, and is used in the crude state in the subsequent syntheses.

EXAMPLE 37

The procedure is as in Example 4, starting with ethyl 2-dimethylamino-6-(4-biphenylyl)-5-methylthio-6-oxo-2,4-hexadienoate, 12N aqueous hydrochloric acid solution (10.7 cc) and ethanol (10.7 cc). The mixture is heated to boiling for 5 minutes, and is then cooled to a temperature of approximately 20° C. After purification by recrystallization in boiling diisopropylether (100 cc), 2-hydroxy-6-(4-biphenylyl)-5-methylthio-6-oxo-2,4-hexadienoate (1.1 g), m.p. 125° C., is obtained.

Ethyl 2-dimethylamino-6-(4-biphenylyl)-5-methylthio-6-oxo-2,4-hexadienoate may be prepared in the following manner:

The procedure is as in Example 4 for the preparation of ethyl 6-phenyl-6-oxo-5-methylthio-2dimethylamino-2,4-hexadienoate, starting with N-(3-dimethylamino)-3-ethoxycarbonylpropenyldiene)-N-methylmethanaminium tetrafluoroborate (6 g), a 2M ethanolic solution of sodium ethylate (10.5 cc) and α-methylthio-4-phenylacetophenone (5.1 g) in ethanol (150 cc). After purification by chromatography on a silica column with a mixture of cyclohexane and ethyl acetate (50:50 by volume) as eluent, ethyl 2-dimethylamino-6-(4-biphenylyl)-5-methylthio-6-oxo-2,4-hexadienoate (2.8 g) is obtained in the form of an orange-coloured oil, and is used in the crude state in the subsequent syntheses.

α-Methylthio-4-phenylacetophenone may be prepared in the following manner:

The procedure is as in example 4 for the preparation of α-methylthioacetophenone, starting with α-bromo-4-phenylacetophenone (9.6 g) and sodium methanethiolate (2.4 g) in ethanol (100 cc). α-Methylthio-4-phenylacetophenone (5.1 g), m.p. 92° C., is obtained, and is used in the crude state in the subsequent syntheses.

EXAMPLE 38

The procedure is as in Example 2, starting with diethyl 2-dimethylamino-5-phenethylthio-2,4-hexadienedioate (22.8 g), 12N aqueous hydrochloric acid solution (120 cc) and ethanol (120 cc). The mixture is heated to boiling for 1 minute, and is then cooled to a temperature of approximately 20° C. After purification by chromatography on a silica column with a mixture of cyclohexane and ethyl acetate (80:20 by volume) as eluent, and recrystallization in boiling cyclohexane (140 cc), diethyl 2-hydroxy-5-phenethylthio-2,4-hexadienedioate (13.2 g), m.p. 50° C., is obtained.

Diethyl 2-dimethylamino-5-phenethylthio-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (20 g), a 2M ethanolic solution of sodium ethylate (42 cc) and ethyl (phenethylthio)acetate (15.7 g) in ethanol (200 cc). Diethyl 2-dimethylamino-5-phenethylthio-2,4-hexadienedioate (22.8 g) is thereby obtained in the form of an orange-coloured oil, and is used in the crude state in the subsequent syntheses.

Ethyl (phenethylthio)acetate may be prepared in the following manner:

The procedure is as in Example 29 for the preparation of ethyl (4-methylbenzylthio)acetate, starting with (2-bromoethyl)benzene (20 g), a 2M ethanolic solution of sodium ethylate (25 cc) and ethyl 2-mercaptoacetate (13 g) in ethanol (150 cc). Ethyl (phenethylthio)acetate (21.7 g) is thereby obtained, and is used in the crude state in the subsequent syntheses.

EXAMPLE 39

1N aqueous sodium hydroxide solution (32 cc) is added in the course of 10 minutes, while a temperature in the region of 20° C. is maintained, to an ethanolic solution of diethyl 2-hydroxy-5-phenethylthio-2,4-hexadienedioate (2.8 g). The mixture is maintained at a temperature in the region of 20° C. for 15 minutes, and is then brought to pH 1 using 1N aqueous hydrochloric acid solution.

The reaction ethanol is evaporated off under reduced pressure (20 mm Hg; 2.7 kPa). After the addition of water (80 cc), the mixture is extracted with ethyl acetate (2×80 cc). The organic phase is dried over anhydrous magnesium sulphate and concentrated to dryness at 40° C. under reduced pressure (20 mm Hg; 2.7 kPa). The solid thereby obtained is recrystallized in a boiling mixture of cyclohexane and ethyl acetate (98:2 by volume). 2-Hydroxy-5-ethoxycarbonyl-5-phenethylthio-2,4-pentadienoic acid (1 g), m.p. 111° C., is thereby obtained.

EXAMPLE 40

The procedure is as in Example 2, starting with diethyl 2-dimethylamino-5-(2-naphthylthio)-2,4-hexadienedioate (11.5 g), 12N aqueous hydrochloric acid solution (58 cc) and ethanol (100 cc). The mixture is heated to boiling for 1 minute, and is then cooled to a temperature of approximately 20° C. After purification by recrystallization in boiling petroleum ether (40°–60° C., 50 cc), diethyl 1-hydroxy-5-(2-naphthylthio)-2,4-hexadienedioate (2 g), m.p. 90° C., is obtained.

Diethyl 2-dimethylamino-5-(2-naphthylthio)-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (10 g), a 2M ethanolic solution of sodium ethylate (21 cc) and ethyl (2-naphthylthio)acetate (12.9 g) in ethanol (100 cc). After purification by chromatography on a silica column with a mixture of cyclohexane and ethyl acetate (50:50 by volume) as eluent, diethyl 2-dimethylamino-5-(2-naphthylthio)-2,4-hexadienedioate (11.5 g) is obtained in the form of a yellow oil, and is used in the crude state in the subsequent syntheses.

Ethyl (2-naphthylthio)acetate may be prepared in the following manner:

The procedure is as in Example 2 for the preparation of ethyl (phenylthio)acetate, starting with 2-naphthylmercaptan (15 g), a 2M ethanolic solution of sodium ethylate (48 cc) and ethyl bromoacetate (15.7 g) in ethanol (150 cc). Ethyl (2-naphthylthio)acetate (16.67 g) is thereby obtained, and is used in the crude state in the subsequent syntheses.

EXAMPLE 41

The procedure is as in Example 39, starting with diethyl 2-hydroxy-5-(2-naphthylthio)-2,4-hexadienedioate, (2 g), 1N aqueous sodium hydroxide solution (80 cc) and ethanol (100 cc). 2-Hydroxy-5-ethoxycarbonyl-5-(2-naphthylthio)-2,4-pentadienoic acid (1.5 g), m.p. 182° C., is obtained by precipitation in ethanol.

EXAMPLE 42

The procedure is as in Example 2, starting with diethyl 2-dimethylamino-5-(1-naphthyl)-2,4-hexadienedioate (2.2 g), 12N aqueous hydrochloric acid solution (12 cc) and ethanol (50 cc). The mixture is heated to boiling for 1 minute, and is then cooled to a temperature of approximately 20° C. After purification by recrystallization in boiling cyclohexane (30 cc), diethyl 2-hydroxy-5-(1-naphthyl)-2,4-hexadienedioate (0.8 g), m.p. 99° C., is obtained.

Diethyl 2-dimethylamino-5-(1-naphthyl)-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (10 g), a 2M ethanolic solution of sodium ethylate (26 cc) and ethyl 2-(1-naphthyl)acetate (7.5 g) in ethanol (100 cc). After purification by chromatography on a silica column with a mixture of cyclohexane and ethyl acetate (80:20 by volume), diethyl 2-dimethylamino-5-(1-naphthyl)-2,4-hexadienedioate (2.2 g) is obtained in the form of a yellow oil, and is used in the crude state in the subsequent syntheses.

EXAMPLE 43

The procedure is as in Example 4, starting with ethyl 2-dimethylamino-6-(4-dimethylaminophenyl)-5-methylthio-6-oxo-2,4-hexadienoate (5.5 g), 12N aqueous hydrochloric acid solution (38 cc) and ethanol (50 cc). The mixture is heated to boiling for 5 minutes, and is then cooled to a temperature of approximately 20° C. After purification by chromatography on a silica column with a mixture of cyclohexane and ethyl acetate (60:40 by volume), ethyl 6-(4-dimethylaminophenyl)-2-hydroxy-5-methylthio-6-oxo-2,4-hexadienoate (3.9 g) is obtained in the form of a brown oil (Rf=0.2; support: silica gel; eluent: cyclohexane/ethyl acetate 60:40 by volume).

Ethyl 2-dimethylamino-6-(4-dimethylaminophenyl)-5-methylthio-6-oxo-2,4-hexadienoate may be prepared in the following manner:

The procedure is as in Example 4 for the preparation of ethyl 6-phenyl-6-oxo-5-methylthio-2-dimethylamino-2,4-hexadienoate, starting with N-(3-dimethylamino-3-ethoxycarbonylpropenylidene)-N-methylmethanaminium tetrafluoroborate (8.6 g), a 2M ethanolic solution of sodium ethylate (15 cc) and α-methylthio-4-dimethylaminoacetophenone (5.8 g) in ethanol (60 cc). After purification by chromatography on a silica column with a mixture of cyclohexane and ethyl acetate (50:50 by volume) as eluent, ethyl 2-dimethylamino-6-(4-dimethylaminophenyl)-5-methylthio-6-oxo-2,4-hexadienoate (5.5 g) is obtained in the form of an orange-coloured oil, and is used in the crude state in the subsequent syntheses.

α-Methylthio-4-dimethylaminoacetophenone may be prepared in the following manner:

The procedure is as in Example 4 for the preparation of α-methylthioacetophenone, starting with α-bromo-4-dimethylaminoacetophenone (12.5 g) and sodium methanethiolate (3.6 g) in ethanol (65 cc). α-Methylthio-4-dimethylaminoacetophenone (9.7 g), m.p. 65° C., is obtained, and is used in the crude state in the subsequent syntheses.

EXAMPLE 44

The procedure is as in Example 4, starting with diethyl 2-dimethylamino-5-(3-benzoylphenyl)-2,4-hexadienedioate (14 g), 12N aqueous hydrochloric acid solution (52.3 cc) and ethanol (52.3 cc). The mixture is heated to boiling for 5 minutes, and is then cooled to a temperature of approximately 20° C. After purification by chromatography on a silica column with a mixture of cyclohexane and ethyl acetate (50:50 by volume) as eluent, and recrystallization in boiling isopropanol (100 cc), diethyl 2-hydroxy-5-(3-benzoylphenyl)-2,4-hexadienedioate (2.3 g), m.p. 105° C., is obtained.

Diethyl 2-dimethylamino-5-(3-benzoylphenyl)-2,4-hexadienedioate may be prepared in the following manner:

The procedure is as in Example 4 for the preparation of ethyl 6-phenyl-6-oxo-5-methylthio-2-dimethylamino-2,4-hexadienoate, starting with N-(3-dimethylamino-3-ethoxycarbonylpropenylidene)-N-methylmethanaminium tetrafluoroborate (17.8 g), a 2M ethanolic solution of sodium ethylate (31.3 cc) and ethyl (3-benzoylphenyl)acetate (16.8 g) in ethanol (100 cc). After purification by chromatography on a silica column with dichloromethane as eluent, diethyl 2-dimethylamino-5-(3-benzoylphenyl)-2,4-hexadienedioate (14 g) is obtained in the form of a yellow oil, and is used in the crude state in the subsequent syntheses.

Ethyl (3-benzoylphenyl)acetate may be prepared in the following manner:

The procedure is as in Example 33 for the preparation of ethyl (3-phenoxyphenyl)acetate, starting with (3-benzoylphenyl)acetic acid (16.6 g) and 36N aqueous sulphuric acid solution (2 cc) in ethanol (200 cc). Ethyl (3-benzoylphenyl)acetate (16.8 g) is obtained in the form of a brown oil, and is used in the crude state in the subsequent syntheses.

(3-Benzoylphenyl)acetic acid may be prepared according to the method described by G. COMISSO et al., Gass. Chim. Ital. 80, vol. 110, 123 (1977).

EXAMPLE 45

The procedure is in Example 4, starting with diethyl 2-dimethylamino-5-(3-biphenylyl)-2,4-hexadienedioate (4.2 g), 12N aqueous hydrochloric acid solution (17 cc) and ethanol (17 cc). The mixture is heated to boiling for 5 minutes, and is then cooled to a temperature of approximately 20° C. After purification by chromatography on a silica column with dichloromethane as eluent, and recrystallization in boiling cyclohexane (75 cc), diethyl 5-(3-biphenylyl)-2-hydroxy-2,4-hexadienedioate (0.7 g), m.p. 95° C., is obtained.

Diethyl 2-dimethylamino-5-(3-biphenylyl)-2,4-hexadienedioate may be prepared in the following manner:

The procedure is as in Example 4 for the preparation of ethyl 6-phenyl-6-oxo-5-methylthio-2-dimethylamino-2,4-hexadienoate, starting with N-(3-dimethylamino-3-ethoxycarbonylpropenylidene)-N-methylmethanaminium tetrafluoroborate (8 g), a 2M ethanolic solution of sodium ethylate (14 cc) and ethyl 1-(3-biphenylyl)acetate (6.7 g) in ethanol (30 cc). After purification by chromatography on a silica column with dichloromethane as eluent, diethyl 2-dimethylamino-5-(3-biphenylyl)-2,4-hexadienedioate (4.2 g) is obtained in the form of a yellow oil, and is used in the curde state in the subsequent syntheses.

Ethyl 1-(3-biphenylyl)acetate may be prepared in the following manner:

The procedure is as in Example 33 for the preparation of ethyl (3-phenoxyphenyl)acetate, starting with (3-biphenylyl)acetic acid (6.8 g) and 36N aqueous sulphuric acid solution (0.5 cc) in ethanol (50 cc). Ethyl 1-(3-biphenylyl)acetate (6.8 g) is obtained in the form of a brown oil, and is used in the crude state in the subseuqent synthesis.

(3-Biphenylyl)acetic acid may be prepared according to the method described by G. SAM et al., J. Pharm. Sciences, vol. 58, no. 8, 953 (1969).

EXAMPLE 46

The procedure is as in Example 2, starting with diethyl 2-dimethylamino-5-(2-methylbenzylthio)-2,4-hexadienedioate (9.5 g), 12N aqueous hydrochloric acid solution (50 cc) and ethanol (100 cc). The mixture is heated to boiling for 1 minute, and is then cooled to a temperature of approximately 20° C. After purification by recrystallization in boiling cyclohexane (100 cc), diethyl 2-hydroxy-5-(2-methylbenzylthio)-2,4-hexadienedioate (6.9 g), m.p. 95° C., is obtained.

Diethyl 2-dimethylamino-5-(2-methylbenzylthio)-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (10 g), a 2M ethanolic solution of sodium ethylate (21 cc) and ethyl (2-methylbenzylthio)acetate (7.9 g) in ethanol (100 cc). After purification by chromatography on a silica column with a mixture of cyclohexane and ethyl acetate (70:30 by volume) as eluent, diethyl 2-dimethylamino-5-(2-methylbenzylthio)-2,4-hexadienedioate (9.5 g) is obtained in the form of a yellow oil, and is used in the crude state in the subsequent syntheses.

Ethyl (2-methylbenzylthio)acetate may be prepared in the following manner:

The procedure is as in Example 29 for the preparation of ethyl (4-methylbenzylthio)acetate, starting with 2-bromomethyltoluene (10 g), a 2M ethanolic solution of sodium ethylate (30 cc) and ethyl 2-mercaptoacetate (6.5 g), in ethanol (100 cc). Ethyl (2-methylbenzylthio)acetate (8.9 g) is thereby obtained, and is used in the crude state in the subsequent syntheses.

EXAMPLE 47

The procedure is as in Example 2, starting with diethyl 2-dimethylamino-5-(4-isopropylbenzylthio)-2,4-hexadienedioate (8.8 g), 12N aqueous hydrochloric acid solution (44 cc) and ethanol (100 cc). The mixture is heated to boiling for 1 minute, and is then cooled to a temperature of approximately 20° C. After purification by recrystallization in boiling cyclohexane (50 cc), diethyl 2-hydroxy-5-(4-isopropylbenzylthio)-2,4-hexadienedioate (5.6 g), m.p. 86° C., is obtained.

Diethyl 2-dimethylamino-5-(4-isopropylbenzylthio)-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (10 g), a 2M ethanolic solution of sodium ethylate (21 cc) and ethyl (4-isopropylbenzylthio)acetate (8.8 g) in ethanol (100 cc). After purification by chromatography on a silica column with a mixture of cyclohexane and ethyl acetate (80:20 by volume) as eluent, diethyl 2-dimethylamino-5-(4-isopropylbenzylthio)-2,4-hexadienedioate (8.8 g) is obtained in the form of an orange-coloured oil, and is used in the crude state in the subsequent syntheses.

Ethyl (4-isopropylbenzylthio)acetate may be prepared in the following manner:

The procedure is as in Example 29 for the preparation of ethyl (4-methylbenzylthio)acetate, starting with 1-bromomethyl-4-isopropylbenzene (15 g), a 2M ethanolic solution of sodium ethylate (49 cc) and ethyl 2-mercaptoacetate (9.8 g) in ethanol (150 cc). Ethyl (4-isopropylbenzylthio)acetate (17.9 g) is thereby obtained, and is used in the crude state in the subsequent syntheses.

EXAMPLE 48

The procedure is as in Example 4, starting with ethyl 2-dimethylamino-6-(3-chlorophenyl)-5-methylthio-6-oxo-2,4-hexadienoate (7.3 g), 12N aqueous hydrochloric acid solution (30.9 cc) and ethanol (62 cc). The mixture is heated to boiling for 5 minutes, and is then cooled to a temperature of approximately 20° C. After purification by recrystallization in boiling cyclohexane (71 cc), ethyl 6-(3-chlorophenyl)-2-hydroxy-5-methylthio-6-oxo-2,4-hexadienoate (6.6 g), m.p. 90° C., is obtained.

Diethyl 2-dimethylamino-6-(3-chlorophenyl)-5-methylthio-6-oxo-2,4-hexadienedioate may be prepared in the following manner:

The procedure is as in Example 4 for the preparation of ethyl 6-phenyl-6-oxo-5-methylthio-2-dimethylamino-2,4-hexadienoate, starting with N-(3-dimethylamino-3-ethoxycarbonylpropenylidene)-N-methylmethanaminium tetrafluoroborate (11.5 g), a 2M ethanolic solution of sodium ethylate (20 cc) and α-methylthio-3-chloroacetophenone (8 g) in ethanol (80 cc). After purification by chromatography on a silica column with a mixture of cyclohexane and ethyl acetate (50:50 by volume) as eluent, ethyl 2-dimethylamino-6-(3-chlorophenyl)-5-methylthio-6-oxo-2,4-hexadienoate (7.3 g) is obtained in the form of an orange-coloured oil, and is used in the crude state in the subsequent syntheses.

α-Methylthio-3-chloroacetophenone may be prepared in the following manner:

The procedure is as in Example 4 for the preparation of α-methylthioacetophenone, starting with α-bromo-3-chloroacetophenone (22.3 g) and sodium methanethiolate (6.8 g) in ethanol (223 cc). α-Methylthio-3-chloroacetophenone (17.3 g) is thereby obtained, and is used in the crude state in the subsequent syntheses.

EXAMPLE 49

The procedure is as in Example 2, starting with diethyl 2-dimethylamino-5-(3-methylbenzylthio)-2,4-hexadienedioate (11 g), 12N aqueous hydrochloric acid solution (58 cc) and ethanol (100 cc). The mixture is heated to boiling for 1 minute and is then cooled to a temperature of approximately 20° C. After purification by chromatography on a silica column with a mixture of cyclohexane and ethyl acetate (80:20 by volume) as eluent, and recrystallization in boiling cyclohexane (17 cc), diethyl 2-hydroxy-5-(3-methylbenzylthio)-2,4-hexadienedioate (6.6 g), m.p. 78° C., is obtained.

Diethyl 2-dimethylamino-5-(3-methylbenzylthio)-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (10 g), a 2M ethanolic solution of sodium ethylate (21 cc) and ethyl (3-methylbenzylthio)acetate (7.9 g) in ethanol (100 cc). Diethyl 2-dimethylamino-5-(3-methylbenzylthio)-2,4-hexadienedioate (11 g) is obtained in the form of a brown oil, and is used in the crude state in the subsequent syntheses.

Ethyl (3-methylbenzylthio)acetate may be prepared in the following manner:

The procedure is as in Example 29 for the preparation of ethyl (4-methylbenzylthio)acetate, starting with 3-bromomethyltoluene (15 g), a 2M ethanolic solution of sodium ethylate (44.5 cc) and ethyl 2-mercaptoacetate (9.7 g) in ethanol (100 cc). Ethyl (3-methylbenzylthio)acetate (14.4 g) is thereby obtained, and is used in the crude state in the subsequent syntheses.

EXAMPLE 50

The procedure is as in Example 2, starting with diethyl 2-dimethylamino-5-methylthio-2,4-hexadienedioate (21.9 g), 12N aqueous hydrochloric acid solution (114 cc) and ethanol (110 cc). The mixture is heated to boiling for 5 minutes, and is then cooled to a temperature of approximately 20° C. After purification by recrystallization in boiling cyclohexane (100 cc), diethyl 2-hydroxy-5-methylthio-2,4-hexadienedioate (9.7 g), m.p. 80° C., is obtained.

Diethyl 2-dimethylamino-5-methylthio-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (28.6 g), a 2M ethanolic solution of sodium ethylate (50 cc) and ethyl (methylthio)acetate (13.4 g) in ethanol (180 cc). Diethyl 2-dimethylamino-5-methylthio-2,4-hexadienedioate (21.9 g) is thereby obtained in the form of a brown oil, and is used in the crude state in the subsequent syntheses.

Ethyl (methylthio)acetate may be prepared in the following manner:

The procedure is as in Example 2 for the preparation of ethyl (phenylthio)acetate, starting with sodium methanethiolate (7 g) and ethyl bromoacetate (16.7 g) in ethanol (80 cc). Ethyl (methylthio)acetate (13.4 g) is thereby obtained, and is used in the crude state in the subsequent syntheses.

EXAMPLE 51

The procedure is as in Example 2, starting with diethyl 2-dimethylamino-5-ethylthio-2,4-hexadienedioate (8.5 g), 12N aqueous hydrochloric acid solution (60 cc) and ethanol (100 cc). The mixture is stirred for 15 minutes at a temperture of approximately 20° C. After purification by chromtography on a silica column with a mixture of cyclohexane and ethyl acetate (80:20 by volume) as eluent, and recrystallization in boiling cyclohexane (22 cc), diethyl 2-hydroxy-5-ethylthio-2,4-hexadienedioate (4.4 g), m.p. 65° C., is obtained.

Diethyl 2-dimethylamino-5-ethylthio-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (10 g), a 2M ethanolic solution of sodium ethylate (21 cc) and ethyl (ethylthio)acetate (5.2 g) in ethanol (100 cc). Diethyl 2-dimethylamino-5-ethylthio-2,4-hexadienedioate (8.5 g) is thereby obtained in the form of a red oil, and is used in the crude state in the subsequent syntheses.

Ethyl (ethylthio)acetate may be prepared in the following manner:

The procedure is as in Example 29 for the preparation of ethyl (4-methylbenzylthio)acetate, starting with iodoethane (10.5 g), a 2M ethanolic solution of sodium ethylate (37 cc) and ethyl 2-mercaptoacetate (8.1 g) in ethanol (100 cc). Ethyl (ethylthio)acetate (6.9 g) is thereby obtained, and is used in the crude state in the subsequent syntheses.

EXAMPLE 52

The procedure is as in Example 2, starting with 6-ethyl 1-tert-butyl 2-dimethylamino-5-phenylthio-2,4-hexadienedioate (4.7 g), 12N aqueous hydrochloric acid solution (25 cc) and ethanol (50 cc). The mixture is heated to boiling for 1 minute, and is then cooled to a temperature of approximately 20° C. After purification by recrystallization in a boiling mixture (88 cc) of petroleum ether (40°-60° C.) and diisopropyl ether (50:50 by volume), 6-ethyl 1-tert-butyl 2-hydroxy-5-phenylthio-2,4-hexadienedioate (3 g), m.p. 113° C., is obtained.

6-Ethyl 1-tert-butyl 2-dimethylamino-5-phenylthio-2,4-hexadienedioate may be prepared in the following manner:

The procedure is as in Example 2 for the preparation of diethyl 2-dimethylamino-5-phenylthio-2,4-hexadienedioate, starting with N(3-dimethylamino-3-t-butyloxycarbonylpropenylidene)-N-methylmethanaminium tetrafluoroborate (4.05 g), a 1.6M solution (8.8 cc) of butyllithium in hexane and ethyl (phenylthio)acetate (2.8 g) in tetrahydrofuran (65 cc). After purification by chromatography on a silica column with a mixture of cyclohexane and ethyl acetate (70:30 by volume) as eluent, 6-ethyl 1-tert-butyl 2-dimethylamino-5-phenylthio-2,4-hexadienedioate (2.6 g), m.p. 85°-88° C., is obtained.

N-(3-Dimethylamino-3-t-butyloxycarbonylpropenylidene)-N-methylmethanaminium tetrafluoroborate may be obtained in the following manner:

The procedure is as in Example 2 for the preparation of N-(3-dimethylamino-3-ethoxycarbonylpropenylidene)-N-methylmethanaminium tetrafluoroborate, starting with N-(3-ethoxy-3-t-butyloxycarbonyl-dipropenylidene)-N-methylmethanaminium tetrafluoroborate (5.2 g) and dimethylamine (1.1 cc) dissolved in dichloromethane (8 cc). After separation by filtration, N-(3-dimethylamino-3-t-butyloxycarbonylpropenylidene)-N-methylmethanaminium tetrafluoroborate (4.1 g), m.p. 137° C., is obtained.

N-(3-Ethoxy-3-t-butyloxycarbonylpropenylidene)-N-methylmethanaminium tetrafluoroborate may be obtained in the following manner:

The procedure is as in Example 2 for the preparation of N-(3-ethoxy-3-ethoxycarbonylpropenylidene)-N-methylmethanaminium tetrafluoroborate, starting with t-butyl 4-dimethylamino-2-oxo-3-butenoate (3.3 g) and triethyloxonium tetrafluoroborate (3.62 g) in dichloromethane (20 cc). The solution of N-(3-ethoxy-3-t-butyloxycarbonylpropenylidene)-N-methylmethanaminium tetrafluoroborate in methylene chloride thereby obtained is stored under an argon atmosphere and used immediately in the subsequent syntheses.

t-Butyl 4-dimethylamino-2-oxo-3-butenoate may be obtained in the following manner:

The procedure is as in Example 2 for the preparation of ethyl 4-dimethylamino-2-oxo-3-butenoate, starting with t-butylpyruvate (9.7 g) and N,N-dimethylformamide diethyl acetal (11.4 g). After purification by chromatography on a silica column with ethyl acetate as eluent, and recrystallization in boiling diisopropyl ether (50 cc), t-butyl 4-dimethylamino-2-oxo-3-butenoate (3.3 g), m.p. 93° C., is obtained.

t-Butyl pyruvate may be prepared according to the method described by H. C. BROWN et al., J. Org. Chem., 50, 1384 (1950).

EXAMPLE 53

The procedure is as in Example 2, starting with diethyl 2-dimethylamino-5-n-butylthio-2,4-hexadienedioate (10 g), 12N aqueous hydrochloric acid solution (63 cc) and ethanol (100 cc). The mixture is maintained for 1 hour at a temperature of approximately 20° C. After purification by chromatography on a silica column with dichloromethane as eluent, diethyl 2-hydroxy-5-n-butylthio-2,4-hexadienedioate (5.6 g), m.p. 37° C., is obtained. Diethyl 2-dimethylamino-5-n-butylthio-2,4-hexadienedioate may be prepared in the following manner:

The procedure is as in Example 2 for the preparation of diethyl 2-dimethylamino-5-phenylthio-2,4-hexadienedioate, starting with N-(dimethylamino-3-ethoxycarbonylpropenylidene)-N-methylmethanaminium tetrafluoroborate (10 g), a 2M ethanolic solution of sodium ethylate (17.5 cc) and ethyl (n-butyolthio)acetate (6.16 g) in ethanol (60 cc). Diethyl 2-dimethylamino-5-n-butylthio-2,4-hexadienedioate (10 g) is thereby obtained in the form of an orange-red oil, and is used in the crude state in the subsequent syntheses.

Ethyl (n-butylthio)acetate may be prepared in the following manner:

The procedure is as in Example 2 for the preparation of ethyl (phenylthio)acetate, starting with n-butylmercaptan (10.7 cc), a 2M ethanolic solution of sodium ethylate (50 cc) and ethyl bromoacetate (16.7 g) in ethanol (100 cc). Ethyl (n-butylthio)acetate (15.4 g) is thereby obtained, and is used in the crude state in the subsequent syntheses.

EXAMPLE 54

The procedure is as in Example 2, starting with diethyl 2-dimethylamino-5-isopropylthio-2,4-hexadienedioate (9.8 g), 12N aqueous hydrochloric acid solution (63 cc) and ethanol (98 cc). The mixture is stirred for 1 hour at a temperature of approximately 20° C. After purification by recrystallization in boiling pentane (90 cc), diethyl 2-hydroxy-5-isopropylthio-2,4-hexadienedioate (5.3 g), m.p. 68° C., is obtained.

Diethyl 2-dimethylamino-5-isopropylthio-2,4-hexadienedioate may be prepared in the following manner:

The procedurre is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (10 g), a 2M ethanolic solution of sodium ethylate (17.5 cc) and ethyl (isopropylthio)acetate (5.7 g) in ethanol (57 cc). Diethyl 2-dimethylamino-5-isopropylthio-2,4-hexadienedioate (9.8 g) is thereby obtained in the form of an orange-coloured oil, and is used in the crude state in the subsequent syntheses.

Ethyl (isopropylthio)acetate may be prepared in the following manner: The procedure is as in Example 2 for the preparation of ethyl (phenylthio)acetate, starting with isopropylmercaptan (9.3 cc), a 2M ethanolic solution of sodium ethylate (50 cc) and ethyl bromoacetate (11.1 cc) in ethanol (100 cc). Ethyl (isopropylthio)acetate (14 g) is thereby obtained, and is used in the crude state in the subsequent syntheses.

EXAMPLE 55

The procedure is as in Example 2, starting with ethyl 5-dimethylamino-5-phenyl-2-phenethylthio-2,4-pentadienoate (4.5 g), 12N aqueous hydrochloric acid solution (23.6 cc) and ethanol (45 cc). The mixture is stirred for 3 hours at a temperature of approximately 20° C. After purification by chromatography on a silica column with dichloromethane as eluent, ethyl 5-oxo-5-phenyl-2-phenethylthio-2-pentenoate (2.8 g) is obtained in the form of a yellow oil (Rf=0.4; support: silica gel; eluent: dichloromethane).

Ethyl 5-dimethylamino-5-phenyl-2-phenethylthio-2,4-pentadienoate may be prepared in the following manner:

The procedure is as in Example 24 for the preparation of ethyl 5-dimethylamino-5-phenyl-2-phenylthio-2,4-pentadienoate, starting with N-(3-dimethylamino-3-phenylpropenylidene)-N-methylmethanaminium tetrafluoroborate (5.8 g), a 2M ethanolic solution of sodium ethylate (10 cc) and ethyl (phenethylthio)acetate (4.5 g) in ethanol (50 cc). After purification by chromatography on a silica column with dichloromethane as eluent, ethyl 5-dimethylamino-5-phenyl-2-phenethylthio-2,4-pentadienoate (4.5 g) is obtained in the form of a yellow oil, and is used in the crude state in the subsequent syntheses.

EXAMPLE 56

The procedure is as in Example 2, starting with ethyl 5-dimethylamino-5-benzoyl-2-phenylthio-2,4-pentadienoate (4 g), 12N aqueous hydrochloric acid solution (21 cc) and ethanol (40 cc). The mixture is heated to boiling for 3 minutes, and is then cooled to a temperature of approximately 20° C. After purification by recrystallization in boiling cyclohexane (70 cc), ethyl 5-hydroxy-6-oxo-6-phenyl-2-phenylthio-2,4-hexadienoate (2.9 g), m.p. 110° C., is obtained.

Ethyl 5-dimethylamino-5-benzoyl-2-phenylthio-2,4-pentadienoate may be prepared in the following manner:

The procedure is as in Example 2 for the preparation of diethyl 2-dimethylamino-5-phenylthio-2,4-hexadienedioate, starting with N-(3-dimethylamino-3-benzoylpropenylidene)-N-methylmethanaminium tetrafluoroborate (5 g), a 2M ethanolic solution of sodium ethylate (7.9 cc) and ethyl (phenylthio)acetate (3.1 g) in ethanol (50 cc). After purification by chromatography on a silica column with a mixture of cyclohexane and ethyl acetate (80:20 by volume) as eluent, ethyl 5-dimethylamino-5-benzoyl-2-phenylthio-2,4-pentadienoate (4.1 g), m.p. 58° C., is obtained.

N-(3-Dimethylamino-3-benzoylpropenylidene)-N-methylmethanaminium tetrafluoroborate may be prepared in the following manner:

The procedure is as in Example 24 for the preparation of N-(3-dimethylamino-3-phenylpropenylidene)-N-methylmethanaminium tetrafluoroborate, starting with 4-dimethylamino-1-phenyl-3-butene-1,2-dione (9.3 g), triethyloxonium tetrafluoroborate (10.3 g) and dimethylamine (3.2 cc) in dichloromethane (140 cc). After precipitation in ethyl acetate (30 cc), N-(3-dimethylamino-3-benzoylpropenylidene)-N-methylmethanaminium tetrafluoroborate (5 g), m.p. 140° C., is obtained.

4-dimethylamino-1-phenyl-3-butene-1,2-dione may be prepared in the following manner:

The procedure is as in Example 2 for the preparation of ethyl 4-dimethylamino-2-oxo-3-butenoate, starting with 1-phenyl-1,2-propanedione (25 g) and N,N-dimethylformamide diethyl acetal (28.3 g). After purification by chromatography on a silica column with ethyl acetate as eluent, 4-dimethylamino-1-phenyl-3-butene-1,2-dione (9.3 g), m.p. 88° C., is obtained.

EXAMPLE 57

The procedure is as in Example 2, starting with diethyl 2-dimethylamino-5-(2,4,6-trimethylbenzylthio)-2,4-hexadienedioate (6.4 g), 12N aqueous hydrochloric acid solution (32 cc) and ethanol (80 cc). The mixture is stirred for 90 minutes at a temperature of approximately 20° C. After purification by recrystallization in boiling cyclohexane (100 cc), diethyl 2-hydroxy-5-(2,4,6-trimethylbenzylthio)-2,4-hexadienedioate (4.28 g), m.p. 122° C., is obtained.

Diethyl 2-dimethylamino-5-(2,4,6-trimethylbenzylthio)-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (10 g), a 2M ethanolic solution of sodium ethylate (21 cc) and ethyl (2,4,6-trimethylbenzylthio)acetate (8.8 g) in ethanol (80 cc). After purification by chromatography on a silica column with a mixture of cyclohexane and ethyl acetate (70:30 by volume) as eluent, diethyl 2-dimethylamino-5-(2,4,6-trimethylbenzylthio)-2,4-hexadienedioate (6.44 g) is obtained in the form of a yellow oil, and is used in the crude state in the subsequent syntheses.

Ethyl (2,4,6-trimethylbenzylthio)acetate may be prepared in the following manner:

The procedure is as in Example 29 for the preparation of ethyl (4-methylbenzylthio)acetate, starting with 2,4,6-trimethylbenzyl chloride (10.25 g), a 2M ethanolic solution of sodium ethylate (32.5 cc) and ethyl 2-mercaptoacetate (7.1 g) in ethanol (150 cc). Ethyl (2,4,6-trimethylbenzylthio)acetate (11 g) is thereby obtained, and is used in the crude state in the subsequent syntheses.

EXAMPLE 58

The procedure is as in Example 2, starting with diethyl 2-dimethylamino-5-(2-naphthylmethanethio)-2,4-hexadienedioate (9 g), 12N aqueous hydrochloric acid solution (42 cc) and ethanol (100 cc). The mixture is heated to boiling for 1 minute, and is then cooled to a temperature of approximately 20° C. After purification by recrystallization in boiling cyclohexane (100 cc), diethyl 2-hydroxy-5-(2-naphthylmethanethio)-2,4-hexadienedioate (7 g), m.p. 88° C., is obtained.

Diethyl 2-dimethylamino-5-(2-naphthylmethanethio)-2,4-hexadienedioate may be prepared in the following manner:

The procedure is as in Example 2 for the preparation of diethyl 2-dimethylamino-5-phenylthio-2,4-hexadienedioate, starting with N-(3-dimethylamino-3-ethoxycarbonylpropenylidene)-N-methylmethanaminium tetrafluoroborate (10 g), a 2M ethanolic solution of sodium ethylate (21 cc) and ethyl (2-naphthylmethanethio)acetate (9.1 g) in ethanol (100 cc). After purification by chromatography on a silica column with a mixture of cyclohexane and ethyl acetate (80:20 by volume) as eluent, diethyl 2-dimethylamino-5-(2-naphthylmethanethio)-2,4-hexadienedioate (9 g) is obtained in the form of a yellow oil, and is used in the crude state in the subsequent syntheses.

Ethyl (2-naphthylmethanethio)acetate may be prepared in the following manner:

The procedure is as in Example 29 for the preparation of ethyl (4-methylbenzylthio)acetate, starting with 2-bromomethylnaphthalene (20 g), sodium hydride (5.1 g) in a 50% strength dispersion in liquid paraffin and ethyl 2-mercaptoacetate (10.9 g) in tetrahydrofuran (200 cc). After purification by chromatography on a silica column with a mixture of cyclohexane and ethyl acetate (80:20 by volume) as eluent, ethyl (2-naphthylmethylthio)acetate (12 g) is obtained, and is used in the crude state in the subsequent syntheses.

The pharmaceutical compositions according to the invention consist of a compound of formula (I), in combination with any other pharmaceuticaly compatible product, which can be inert or physiologically active. These medicinal products according to the invention may be used orally, parenterally, rectally or topically.

As solid compositions for oral administration, tablets, pills, powders (gelatin capsules, wafer tablets) or granules may be used. In these compositions, the active principle according to the invention is mixed with one or more inert diluents such as starch, cellulose, sucrose, lactose or silica. These compositions can also comprise substances other than diluents, e.g. one or more lubricants such as magnesium stearate or talc, a colouring, a coating (dragees) or a lacquer.

As liquid compositions for oral administration, it is possible to use solutions, suspensions, emulsions, syrups and elixirs which are pharmaceutically acceptable, containing inert diluents such as water, ethanol, glycerol, vegetable oils or paraffin oil. These compositions can comprise substances other than diluents, e.g. wetting, sweetening, thickening, flavouring or stabilizing products.

The sterile compositions for parenteral administration are preferably suspensions, emulsions or non-aqueous solutions. As solvent or vehicle, water, propylene glycol, a polyethylene glycol, vegetable oils, especially olive oil, injectable organic esters, eg. ethyl oleate, or other suitable organic solvents can be used. These compositions can also contain adjuvants, especially wetting agents, tonicity-regulating agents, emulsifiers, dispersants and stabilizers. The sterilization can be carried out in several ways, e.g. by aseptic filtration, by incorporating sterilizing agents in the composition, by irradiation or by heating. They can also be prepared in the form of sterile solid compositions which can be dissolved at the time of use in a sterile injectable medium.

The compositions for rectal administration are suppositories or rectal capsules, which contain, apart from the active product, excipients such as cocoa butter, semi-synthetic glycerides or polyethylene glycols.

The compositions for topical administration can be, e.g. creams, ointments, lotions, eyewashes, mouthwashes, nasal drops or aerosols.

In human therapy, the compounds according to the invention are especially useful as anti-inflammatories, as protective agents, in particular, with respect to the gastrointestinal tract, and for the treatment of asthma, allergic conditions, psoriasis, rhumatoid arthritis and fibrosis, in particular hepatic fibrosis.

The doses depend on the effect sought, on the treatment period and on the administration route used; they are generally between 0.1 g and 5 g per day orally for an adult, with unit doses ranging from 20 to 200 mg of active substance.

Generally speaking, the doctor will determine the appropriate dosage in accordance with the age and weight and all other factors specific to the subject to be treated.

The examples which follow illustrate compositions according to the invention:

EXAMPLE A

Gelatin capsules containing a 50-mg dose of active product and having the following composition are prepared according to the customary technique:

| | |
|---|---|
| Ethyl 2-hydroxy-5-methylthio-6-oxo-6-(4-piperidinophenyl)-2,4-hexadienedioate | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets containing a 50-mg dose of active product and having the following composition are prepared according to the customary technique:

| | |
|---|---|
| Ethyl 5-hydroxy-2-phenylthio-2,4-pentadienoate | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerin and titanium oxide (72:3.5:24.5) qs 1 finished film-coated tablet weighing | 245 mg |

EXAMPLE C

An injectable solution containing 10 mg of active product and having the following composition is prepared:

| | |
|---|---|
| 2-Hydroxy-5-phenylthio-5-ethoxycarbonyl-2,4-pentadienoic acid | 10 mg |
| Benzoic acid | 80 mg |
| Benzyl alcohol | 0.06 cc |
| Sodium benzoate | 80 mg |
| Ethanol, 95% strength | 0.4 cc |
| Sodium hydroxide | 24 mg |
| Propylene glycol | 1.6 cc |
| Water qs | 4 cc |

We claim:

1. A substituted alkadiene of formula:

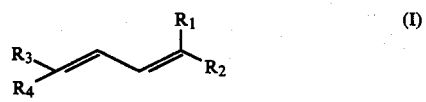

(I)

in which $R_1$ denotes hydroxy or acetoxy, $R_2$ denoted hydrogen, carboxy, alkoxycarbonyl, phenyl or benzoyl, and $R_3$ denotes alkoxycarbonyl or cycloalkyloxycarbonyl in which the cycloalkyl portion contains 3 to 6 carbon atoms, and $R_4$ denotes (a) alkylthio, (b) naphthylmethanethio, (c) benzylthio, (d) benzylthio substituted by one or more alkyls or by trifluoromethyl, phenyl or phenoxy, (e) phenylthio, (f) phenylthio substituted by halogen or alkoxy, (g) naphthylthio, (h) phenethylthio or (i) allylthio, with the proviso that except where otherwise stated in the definitions above, the alkyl and alkoxy radicals and alkyl and alkoxy portions contain 1 to 4 carbon atoms each in a straight or branched chain, and the tautomeric forms of the said substituted alkadienes when $R_1$ denotes hydroxy.

2. A substituted alkadiene according to claim 1 in which $R_1$ denotes hydroxy or acetoxy, $R_2$ denotes hydrogen, carboxy, alkoxycarbonyl or phenyl, $R_3$ denotes alkoxycarbonyl and $R_4$ denotes alkylthio, benzylthio, or benzylthio substituted by alkoxy, and its tautomeric forms when $R_1$ denotes hydroxy.

3. A substituted alkadiene according to claim 1 which is 2-hydroxy-5-phenylthio-5-ethoxycarbonyl-2,4-pentadienoic acid.

4. A substituted alkadiene according to claim 1 which is diethyl 2-hydroxy-5-(4-methoxyphenylthio)-2,4-hexadienedioate.

5. A substituted alkadiene according to claim 1 which is diethyl 5-benzylthio-2-hydroxy-2,4-hexadienedioate.

6. A substituted alkadiene according to claim 1 which is ethyl 5-hydroxy-2-phenylthio-2,4-pentadienoate.

7. A substituted alkadiene according to claim 1 which is diethyl 2-acetoxy-5-phenylthio-2,4-hexadienedioate.

8. A substituted alkadiene according to claim 1 which is ethyl 5-oxo-5-phenyl-2-phenylthio-2-pentenoate.

9. A substituted alkadiene according to claim 1 which is diethyl 2-hydroxy-5-methylthio-2,4-hexadienedioate.

10. A substituted alkadiene according to claim 1 which is diethyl 2-hydroxy-5-ethylthio-2,4-hexadienedioate.

11. A pharmaceutical composition containing at least one activwe substance according to claim 1 and one or more compatible and pharmaceutically acceptable diluents or adjuvants.

* * * * *